(12) United States Patent
Kimura

(10) Patent No.: US 7,717,914 B2
(45) Date of Patent: May 18, 2010

(54) TREATMENT DEVICE

(75) Inventor: Kenichi Kimura, Hachioji (JP)

(73) Assignee: Olympus Medical Systems Corporation, Tokyo (JP)

( * ) Notice: Subject to any disclaimer, the term of this patent is extended or adjusted under 35 U.S.C. 154(b) by 776 days.

(21) Appl. No.: 11/484,823

(22) Filed: Jul. 11, 2006

(65) Prior Publication Data

US 2008/0015567 A1     Jan. 17, 2008

(51) Int. Cl.
*A61B 18/18* (2006.01)
(52) U.S. Cl. ...................................... 606/51
(58) Field of Classification Search .............. 606/41, 606/50, 51
See application file for complete search history.

(56) References Cited

U.S. PATENT DOCUMENTS

| | | | | |
|---|---|---|---|---|
| 5,702,390 A * | 12/1997 | Austin et al. | | 606/48 |
| 5,891,142 A * | 4/1999 | Eggers et al. | | 606/51 |
| 6,126,658 A * | 10/2000 | Baker | | 606/51 |
| 6,527,767 B2 * | 3/2003 | Wang et al. | | 606/32 |
| 6,736,813 B2 * | 5/2004 | Yamauchi et al. | | 606/48 |
| 7,329,257 B2 * | 2/2008 | Kanehira et al. | | 606/52 |
| 7,353,068 B2 * | 4/2008 | Tanaka et al. | | 700/17 |
| 2001/0037109 A1 | 11/2001 | Yamauchi et al. | | |
| 2003/0109876 A1 | 6/2003 | Yamauchi | | |
| 2003/0144652 A1 | 7/2003 | Baker et al. | | |
| 2003/0199869 A1 | 10/2003 | Johnson et al. | | |

FOREIGN PATENT DOCUMENTS

| | | |
|---|---|---|
| EP | 1 568 330 A1 | 8/2005 |
| EP | 1 632 192 A1 | 3/2006 |
| WO | WO 2004/032777 A1 | 4/2004 |

* cited by examiner

*Primary Examiner*—Roy D Gibson
(74) *Attorney, Agent, or Firm*—Scully, Scott, Murphy & Presser, P.C.

(57) ABSTRACT

A treatment device of this invention has a pair of first, second jaws capable of opening/closing with respect to each other at the tip end portion and comprises a tissue pressing portion in the relatively dull shape provided on a surface portion of the first jaw opposite to the second jaw and having a projection portion formed projecting toward the second jaw side, a receiving member provided on a surface portion of the second jaw opposite to the first jaw at a position opposite to the tissue pressing portion, and a plurality of electrode portions provided at least at one of the first jaw and the second jaw so that a high-frequency current flows through a living tissue compressed by the tissue pressing portion and the receiving member.

4 Claims, 30 Drawing Sheets

TREATMENT DEVICE

BACKGROUND OF THE INVENTION

1. Field of the Invention

The present invention relates to a treatment device or more particularly to a treatment device for coagulation, incision, ablation or the like of a living tissue using high-frequency energy while gripping the living tissue between a pair of jaws capable of opening/closing.

2. Description of the Related Art

As a therapeutic treatment method in a surgery under endoscope or an abdominal surgery, a method for performing a therapeutic treatment using a treatment device, for example, has been known.

Such a treatment device is capable of treatment such as coagulation, incision, ablation or the like of a living tissue using high-frequency energy while gripping the living tissue between a pair of jaws capable of opening/closing when energy for treatment to the living tissue is high-frequency energy, for example.

In this type of treatment devices, a number of proposals have been made for efficient treatments including coagulation, incision, ablation or the like of a living tissue.

For example, the specification of US Patent No. 2003/0199869A1 discloses a technology relating to a treatment instrument comprising a pair of jaws capable of opening/closing at the tip end portion and a knife movable between slots formed at the respective jaws.

In such a treatment device, a sealing surface for coagulating the living tissue by applying high-frequency energy and pressure is provided at the respective jaws, and at treatment of the living tissue, the living tissue is coagulated by supplying the high-frequency energy while the living tissue is gripped between the sealing surfaces and then, incision of the living tissue portion coagulated by cutting edge formed by the knife is performed by operating the knife in the distal direction (specifically, forward in the insertion axis direction of the tip end portion).

SUMMARY OF THE INVENTION

In brief, a treatment device of the present invention has a pair of first and second jaws capable of opening/closing with respect to each other at a tip end portion and comprises a tissue pressing portion in the relatively blunt shape having a projection portion provided on a surface portion of the first jaw opposite to the second jaw and formed projecting toward the second jaw side, a receiving member provided at a position opposite to the tissue pressing portion on the surface portion of the second jaw opposite to the first jaw, and a plurality of electrode portions provided at least one of the first jaw and the second jaw so that a high-frequency current flows through the living tissue compressed between the tissue pressing portion and the receiving member.

DESCRIPTION OF THE PREFERRED EMBODIMENTS

Embodiments of the present invention will be described below referring to the attached drawings.

Embodiment 1

Figure 1:
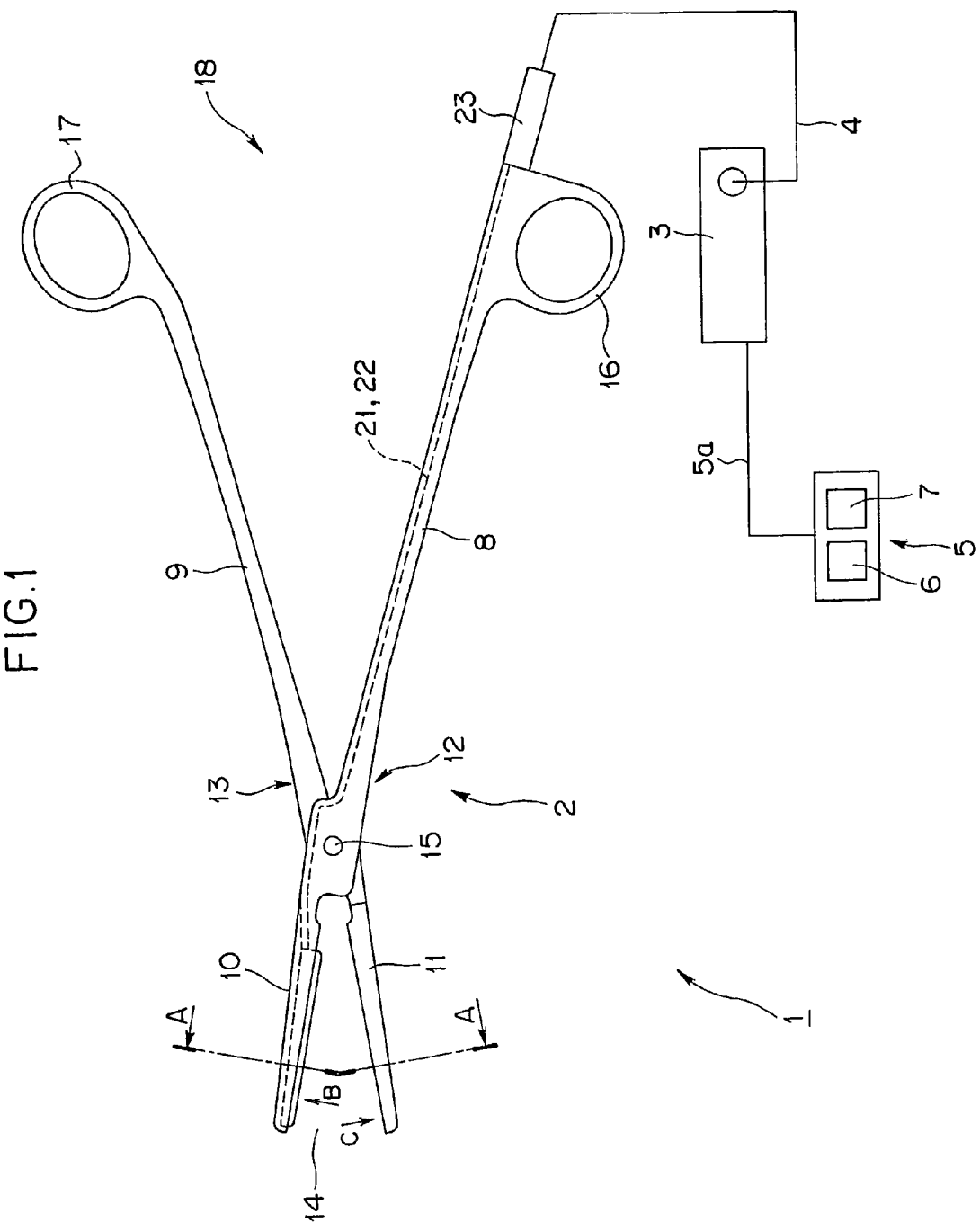
FIG. 1 is a side view showing an entire construction of a treatment device according to an embodiment 1 of the present invention.
Figure 2:
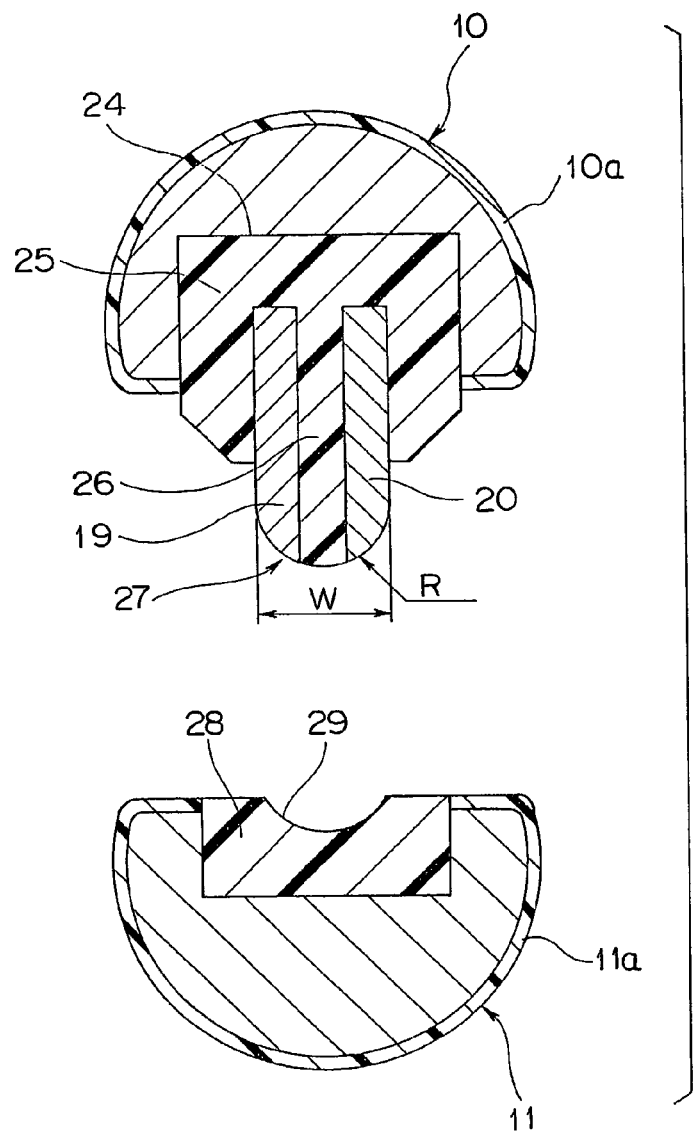
FIG. 2 is a sectional view taken on A-A line in FIG. 1.
Figure 3:
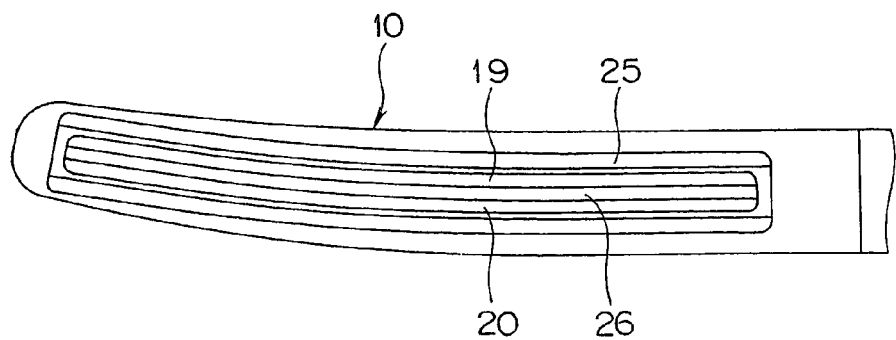
FIG. 3 is a configurational view of a jaw seen from the arrow B direction in FIG. 1.
Figure 4:
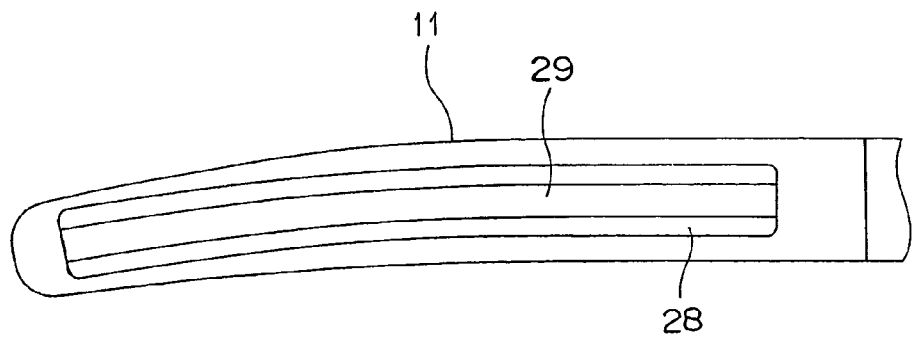
FIG. 4 is a configurational view of the other jaw seen from the arrow C direction in FIG. 1.
Figure 5:
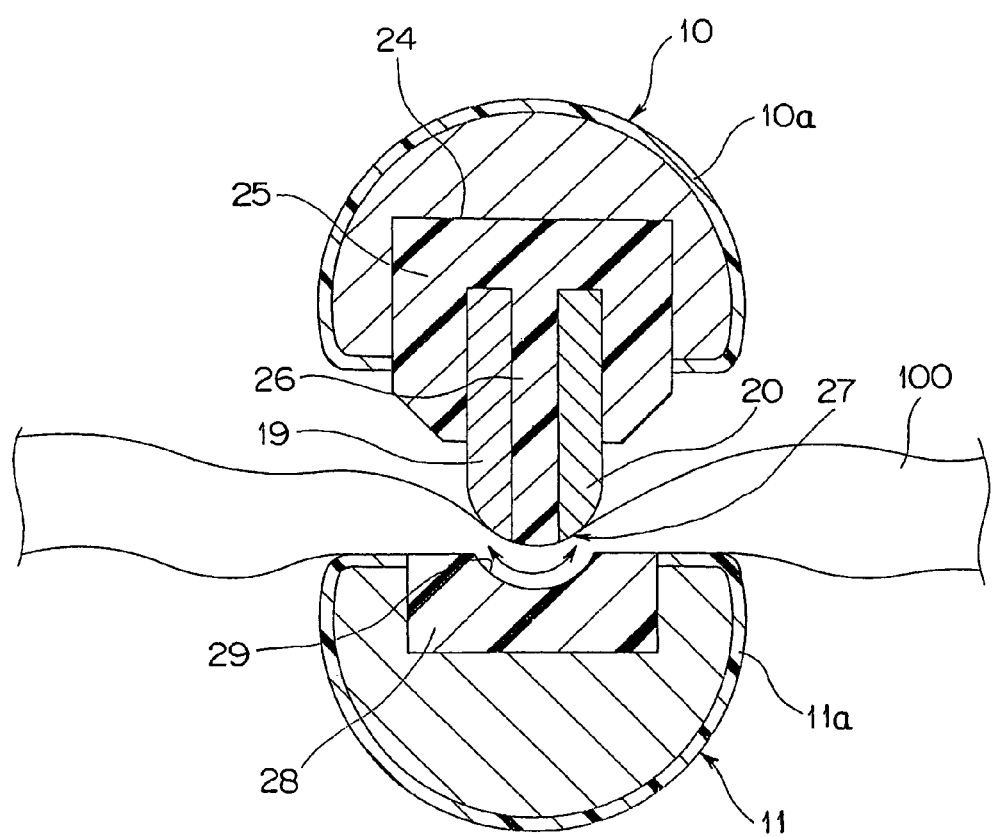
FIG. 5 is an explanatory view for explaining a treatment of a living tissue by the treatment device in FIG. 1.

FIGS. 1 to 5 relate to an embodiment 1 of the present invention, in which FIG. 1 is a side view showing an entire construction of a treatment device according to the embodiment 1, FIG. 2 is a sectional view taken on A-A line in FIG. 1, FIG. 3 is a configurational view of a jaw seen from the arrow B direction in FIG. 1, FIG. 4 is a configurational view of the other jaw seen from the arrow C direction in FIG. 1, and FIG. 5 is an explanatory view for explaining a treatment of a living tissue by the treatment device in FIG. 1.

In the embodiments according to the present invention, high-frequency energy (electric energy) is used as energy for treatment of a living tissue, and a case of construction as a high-frequency treatment device for performing treatments such as coagulation of a living tissue, incision, ablation of the living tissue or the like using this high-frequency energy will be explained.

As shown in FIG. 1, a treatment device 1 according to the embodiment 1 comprises forceps 2 and a high-frequency cautery power supply device (hereinafter abbreviated simply as a power supply device) 3 detachably connected to the forceps 2, for driving/controlling the forceps 2 by outputting a high-frequency power, which is a power supply power, to the forceps 2.

The forceps 2 has a connector provided at a rear end of a connection cord 4 extending from the hand side detachably connected to the power supply device 3. And to this power supply device 3, a foot switch 5 is electrically connected through a connection cord 5a.

The foot switch 5 comprises, for example, a first operation pedal 6 for instructing operation to turn on/off of a coagulation incision mode for performing coagulation and incision of a living tissue and a second operation pedal 7 for instructing operation of turning on/off of a coagulation mode for coagulating the living tissue.

The foot switch 5 generates an operation signal when the first and the second pedals 6, 7 are operated and outputs it to the power supply device 3 through the connection cord 5a. And the power supply device 3 controls on/off of a high-frequency power to be supplied to the forceps 2 based on the operation signal from the foot switch 5. That is, on/off of the high-frequency power to the forceps 2 is controlled by the power supply device 3 when an operator operates on/off of the first pedal 6 or the second pedal 7 of the foot switch 5.

The coagulation/incision mode is a mode that, if the living tissue is a blood vessel, for example, a high-frequency power is supplied that is required for coagulation and hemostasis of a predetermined range of the blood vessel and then, for incision of a coagulated portion of this blood vessel while leaving the both side portions whose bleeding was stopped. The coagulation mode is a mode to supply a high-frequency power required to coagulate and stop bleeding of a predetermined portion of a blood vessel and to bring it to a state not reaching incision.

However, in this embodiment, these modes are not automatically executed by the power supply device 3 but as mentioned above, the coagulation/incision mode or the coagulation mode is executed by the on/off operation of the first pedal 6 or the second pedal 7 of the foot switch 5 while the operator is visually checking the state of coagulation or incision of the living tissue at a treatment of the living tissue.

The forceps 2 mainly comprises a pair of handle portions 8, 9 to be held and operated by the operator, a pair of jaws 10, 11 for gripping the living tissue to be treated for coagulation and incision, and a pair of forceps constituting portions 12, 13 connecting the pair of handle portions 8, 9 and the pair of jaws 10, 11.

The pair of jaws 10, 11 constitute a treatment portion 14 for performing coagulation, incision or the like while gripping the living tissue. The pair of forceps constituting portions 12, 13 are provided between the handle portions 8, 9 and the jaws 10, 11, respectively. And the pair of forceps constituting portions 12, 13 are overlapped with each other with the middle portions substantially crossing each other. Moreover, at the crossing portion where the pair of forceps constituting portions 12, 13 are overlapped with each other, a fulcrum pin 15 for connecting the pair of forceps constituting portions 12, 13 capable of rotational movement is provided. At the pair of handle portions 8, 9, rings 16, 17 for finger insertion are provided in which the fingers of the operator are put.

When the forceps 2 in this construction are opened/closed by inserting the thumb and the fourth finger, for example, in the rings 16, 17 for finger insertion, the pair of jaws 10, 11 are opened/closed in an interlocking manner so that the living tissue is gripped, separated, pressed or ejected. That is, the pair of handle portions 8, 9 and the pair of forceps constituting portions 12, 13 constitute an operation portion 18 of the forceps 2.

The jaw 10 in this embodiment is provided with a first electrode portion 19 and a second electrode portion 20 (See FIG. 2), which will be described later. Inside the forceps constituting portion 12, lead wires 21, 22 electrically connected to the first electrode portion 19 and the second electrode portion 20, respectively, are disposed.

These lead wires 21, 22 extends from the jaw 10 to the handle portion 8 and is electrically connected to the power supply device 3 from a cord connection portion 23 at the rear end side of the ring 16 through the connection cord 4.

Next, a specific construction of the treatment portion 14 of the forceps 2 will be described referring to FIGS. 2 to 4.

As shown in FIGS. 3 and 4, the pair of jaws 10, 11 constituting the treatment portion 14 of the forceps 2 are formed in the tapered shape curved toward the tip end portion. Also, as shown in FIG. 2, a long-groove state recess portion 24 is formed on a surface of the jaw 10 opposite to the other jaw 11. To this recess portion 24, an insulating member 25 formed of an electrically insulating material is fixed.

At this insulating member 25, a wall portion 26 is formed protruding toward the other jaw 11 side. It is to be noted that this insulating member 25 is formed using a material such as ceramics with favorable electrical insulation and high heat resistance (alumina, aluminum nitride, zirconia), plastic (polytetrafluoroethylene (PTFE)), polyether ether ketone (PEEK)), etc. The material is not limited to them but any material with favorable electrical insulation and high heat resistance will do.

Also, as shown in FIGS. 2 and 3, to the insulating member 25, the first electrode portion 19 and the second electrode portion 20 are fixed in the electrically insulated state by the wall portion 26. The first electrode portion 19 and the second electrode portion 20 are arranged along the curved shape in the longitudinal direction of the jaw 10. Suppose here that the first electrode portion 19 is a positive pole in this embodiment, the second electrode portion 20 is a negative pole and high-frequency power flows between these first and second electrode portions 19, 20.

The first electrode portion 19 and the second electrode portion 20 are formed using a metal material such as stainless or copper having electric conductivity. Also, in order to improve electric conductivity, it may be so constituted that the outer surfaces of the first electrode portion 19 and the second electrode portion 20 are coated with gold plating or the like.

The surface of the first electrode portion 19, the second electrode portion 20 and the wall portion 26 opposite to the other jaw 11 (surface portion) is formed as a tissue pressing portion 27 in a relatively dull shape, an arc, for example. In this case, it is so constructed in this embodiment that the width W of the tissue pressing portion 27 is approximately 2 mm and the radius of an R portion forming the arc shape at the tip end portion is approximately 1 mm. It is needless to say that the numeral values are not limited to them. It is to be noted that the tissue pressing portion 27 constitutes the projection portion.

Also, as shown in FIGS. 2 and 4, a receiving member 28 is integrally provided at the other jaw 11 at a position opposite to the tissue pressing portion 27 of the jaw 10. At this receiving member 28, a groove portion 29 in the substantially same shape as that of the tissue pressing portion 27 is formed. The receiving member 28 is formed using a resin material with favorable electrical insulation and high heat resistance such as polytetrafluoroethylene (PTFE).

Though the pair of jaws 10, 11 in this construction are formed using a metal material such as stainless, the respective outer surfaces are, as shown in FIG. 2, covered and constituted by insulating members 10a, 11a formed of an electrically insulating material (such as polytetrafluoroethylene (PTFE) or alumina).

In this embodiment, the wall portion 26 is integrally constructed with the insulating member 25, but not limited to this, the wall portion 26 may be constructed as a member separate from the insulating member.

Next, action when a living tissue is treated using the treatment device 1 of this embodiment will be described referring to FIGS. 1 to 5.

In use of the treatment device 1 of this embodiment, the operator inserts the two fingers in the rings 16, 17 for finger insertion of the operation portion 18 of the forceps 2 and operates rotational movement of these two rings 16, 17 in the opening direction. By this rotational movement operation of the rings 16, 17, the two jaws 10, 11 of the forceps 2 are opened.

In this state, the operator performs positioning so that a living tissue 100 to be treated is disposed between the opened jaws 10, 11.

Next, the operator operates rotational movement of the two rings 16, 17 in the closing direction in that state to grip the living tissue 100 between the tissue pressing portion 27 and the receiving member 28. At this time, as shown in FIG. 5, the living tissue 100 is gripped between the tissue pressing portion 27 and the receiving member 28 in the strongly compressed state.

After that, the operator grips the living tissue 100 and then, selectively turns on the first operation pedal 6, the second operation pedal 7 of the foot switch 5 so as to start coagulation or incision treatment.

Here, by turning on the first operation pedal 6, the power supply device 3 is driven under a first output condition preset in order to perform the coagulation/incision mode, and by turning on the second operation pedal 7, the power supply device 3 is driven under a second output condition preset in order to perform the coagulation mode.

In this case, in the first output condition in the coagulation/incision mode and the second output condition in the coagulation mode, the high-frequency current (300 kHz to 10 MHz, for example) flows between the two first and the second electrode portions 19, 20 from the power supply device 3 through the connection cord 4, the cord connection portion 23 and the lead wires 21, 21. That is, these forceps 2 function as the bipolar type high-frequency treatment instruments.

Next, more specific action at coagulation and incision in the treatment device of this embodiment will be described.

Suppose that the operator is to perform the coagulation/incision mode by turning on the first operation pedal 6 of the foot switch 5, for example. Then, the power supply device 3 controls to turn on supply of the high-frequency power to the forceps 2. Specifically, the power supply device 3 controls so that the high-frequency current with an incision waveform (continuous sinusoidal wave) flows between the two electrode portions 19, 20.

At this time, the high-frequency current flows through the gripped living tissue 100 along the path as shown by an arrow in FIG. 5. By this, Joule heat is generated locally and continuously. By this Joule heat and the compression force between the tissue pressing portion 27 and the receiving member 28, the living tissue 100 goes through the coagulation process and then, it is incised.

That is, the living tissue 100 reaches a coagulation action temperature and then, reaches to an incision action temperature higher than that. By this, incision can be performed quickly while the living tissue 100 is sufficiently coagulated. In this case, both sides of the incision portion to be incised of the living tissue 100 are left with the coagulated portion whose bleeding was sufficiently stopped.

Also, suppose that the operator performs the coagulation mode by turning on the second operation pedal 7 of the foot switch 5. Then, the power supply device 3 control so that supply of the high-frequency power to the forceps 2 is turned on. Specifically, the power supply device 3 controls so that the high-frequency current with the coagulation waveform (burst waveform) flows between the two electrode portions 19, 20.

At this time, since the high-frequency current flows through the gripped living tissue 100 along the path shown by the arrow in FIG. 5 as mentioned above, Joule heat is generated locally and intermittently. By this Joule heat and the compression force between the tissue pressing portion 27 and the receiving member 28, the living tissue 100 is coagulated.

In this case, since the flowing current is in the coagulation waveform (burst waveform), Joule heat is generated intermittently, and the living tissue 100 does not exceed the incision action temperature higher than the coagulation action temperature after it is reached. That is, the living tissue 100 is not incised, but stronger coagulation is made possible. In this case, the coagulation portion to be coagulated of the living tissue 100 is in the coagulated state having an area whose bleeding is sufficiently stopped.

As mentioned above, by selectively operating the first operation pedal 6, the second operation pedal 7 of the foot switch 5 by the operator, a treatment according to the target living tissue can be performed by one type of forceps 2. That is, in this embodiment, when a tissue containing a relatively thin blood vessel is to be treated, for example, the first operation pedal 6 is operated for coagulation, incision under the first output condition preset for performance of the coagulation/incision mode. Alternatively, when a tissue containing a relatively thick blood vessel is to be treated, it is only necessary that the second operation pedal 7 is operated, and firm coagulation is performed under the second output condition preset for performance of the coagulation mode.

Therefore, according to the embodiment 1, coagulation and incision of the living tissue can be performed in a short time and surely. Moreover, by selecting the output condition, a treatment according to the target living tissue can be performed by one type of forceps 2. Thus, it is possible to save labor to prepare plural types of forceps and to switch the forceps according to the target living tissue. By this, time for surgery can be reduced.

Also, in the embodiment 1, since the living tissue is incised by conducting the high-frequency current between the two electrode portions 19, 20, it is not necessary to perform an incision treatment using a sharp blade of a knife in the conventional technique. That is, since edge will not deteriorate and reuse of the forceps 2 is made possible, costs can be reduced more than conventional examples.

Moreover, the forceps 2 of the embodiment 1 has more freedom in the shape of the treatment portion 14 (the pair of jaws 10, 11) as compared with the case of incision operation by movement of the knife as in the conventional technique. By this, it becomes possible to form the shape of the treatment portion according to applications (curved shape, for example).

In the embodiment 1, the treatment portion 14 may be constructed as shown in variations 1 to 5, which will be described later.

The variations 1 to 5 of the embodiment 1 will be described referring to FIGS. 6 to 10. In FIGS. 6 to 10, the same reference numerals are given to the same components as those in the treatment device in the embodiment 1 and the explanation will be omitted, and only differences will be described.

(Variation 1)

Figure 6:
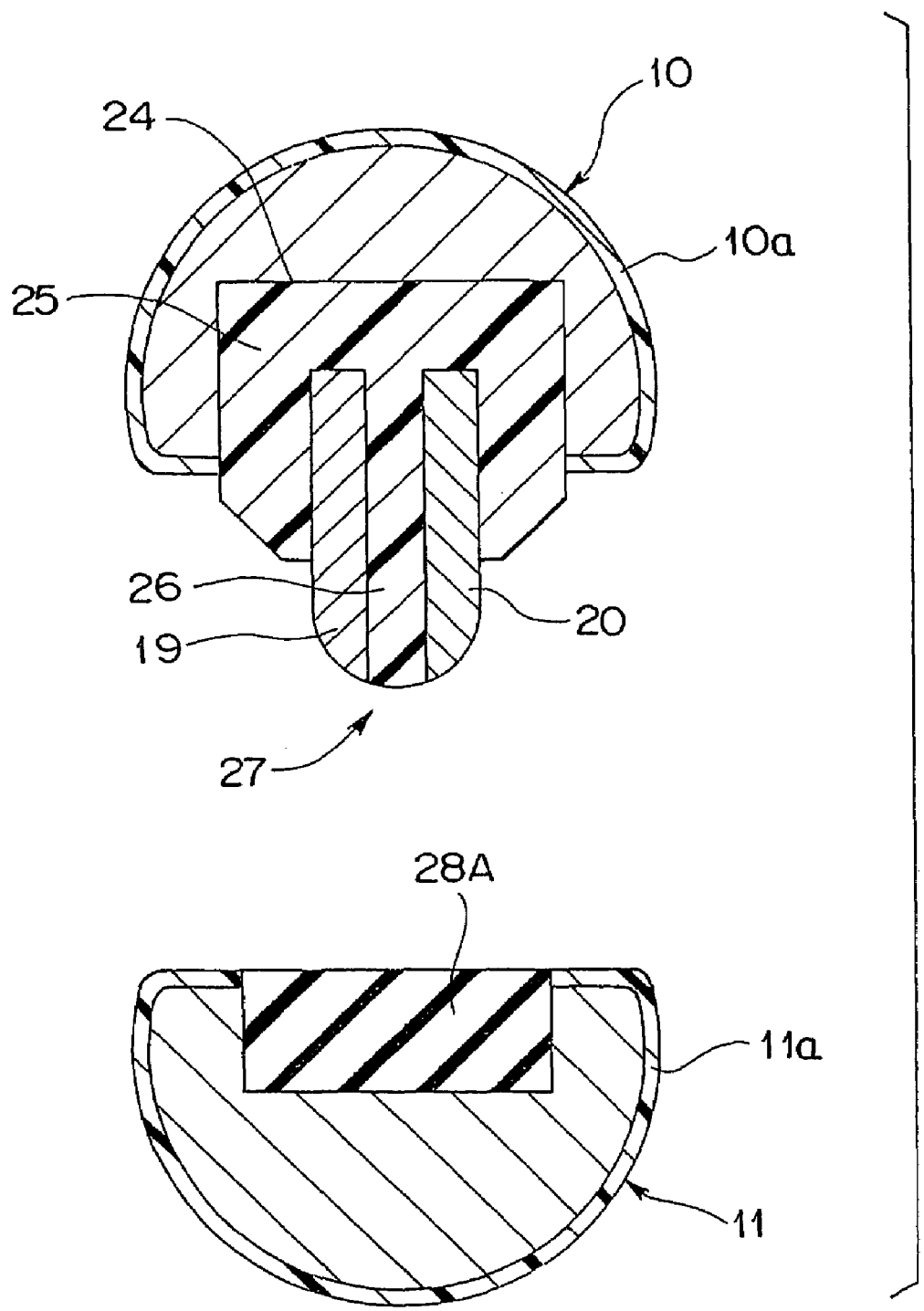
FIG. 6 is a sectional view of a treatment portion showing a variation 1 of the treatment portion in the embodiment 1.

FIG. 6 is a sectional view of a treatment portion showing the variation 1 of the treatment portion in the embodiment 1.

The treatment portion 14 of the embodiment 1 may be constructed as shown in the variation 1 in FIG. 6, for example. That is, as shown in FIG. 6, the jaw 11 constituting the treatment portion 14 comprises a receiving member 28A with a different material in place of the receiving member 28 of the embodiment 1.

This receiving member 28A is integrally provided at a position of the jaw 11 opposite to the tissue pressing portion 27 of the jaw 10. The surface of this receiving member 28A opposite to the tissue pressing member 27 is formed in the plane state.

Moreover, this receiving member 28A is formed of a resin material or an elastic material capable of elastic deformation with favorable electrical insulation and high heat resistance, for example. The receiving member 28A is formed of silicon rubber or fluoro-rubber with JIS A hardness of about 30 to 70°.

The other constructions are the same as those of the embodiment 1.

In the forceps 2 of the so constructed variation 1, the receiving member 28A of the jaw 11 is formed using a resin material or an elastic material capable of elastic deformation.

Therefore, when gripping the living tissue 100 at coagulation, incision treatments, this receiving member 28A is elastically deformed by the compression force between the tissue pressing portion 27 and the receiving member 28A, whereby the living tissue 100 is gripped while being elongated with the elastic deformation of the receiving member 28A.

That is, by elastic deformation of the receiving member 28A, the living tissue 100 is surely gripped between the tissue pressing portion 27 and the receiving member 28A while it is pulled and elongated. Therefore, when the coagulation incision or coagulation treatment is performed by conducting the high-frequency current to the two electrode portions 19, 20 as with the embodiment 1, the coagulation incision or coagulation treatment can be performed in a shorter time than the embodiment 1.

The other actions are the same as those of the embodiment 1.

Therefore, according to the variation 1, since coagulation incision and coagulation treatment performance can be improved in addition to the same effects as those in the embodiment 1, great contribution is made to reduction of time for surgery.

(Variation 2)

Figure 7:
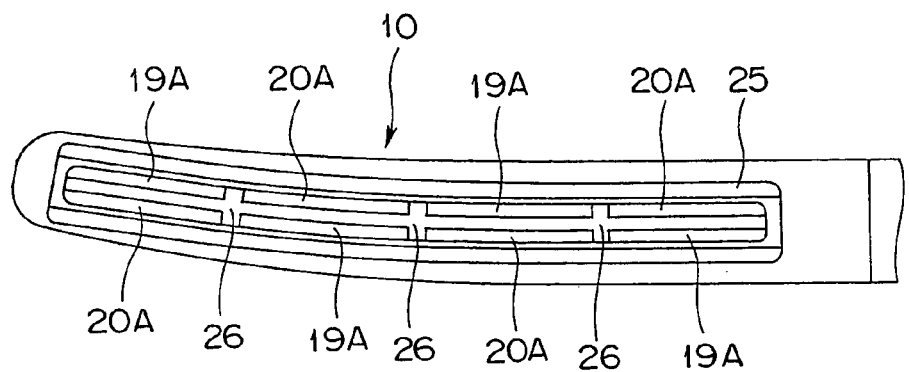
FIG. 7 is a configurational view of the jaw showing a variation 2 of the treatment portion in the embodiment 1.

FIG. 7 is a configurational view of a jaw showing a variation 2 of the treatment device in the embodiment 1.

The treatment portion 14 of the embodiment 1 may be constructed as shown in the variation 2 of FIG. 7, for example. That is, as shown in FIG. 7, the treatment portion 14 of the variation 2 comprises a plurality of first electrode portions 19A and a plurality of second electrode portions 20A in place of the first electrode portion 19 and the second electrode portion 20 in the embodiment 1.

The plurality of first electrode portions 19A and the plurality of second electrode portions 20A are provided at the insulating member 25 as in the embodiment 1.

In this case, the plurality of first electrode portions 19A and the plurality of second electrode portions 20A are fixed in the state electrically insulated by the wall portion 26 of the insulating member 25, respectively. Also, the plurality of first electrode portions 19A and the plurality of second electrode portions 20A are fixed while changing the arrangement positions alternately in the longitudinal direction (axial direction of the forceps 2) of the forceps 2, and in the direction orthogonal to the longitudinal direction of the forceps 2 (the direction orthogonal to the axial direction of the forceps 2), each of the first electrode portions 19A and the second electrode portions 20A are arranged side by side to be opposed to each other. Moreover, the plurality of first electrode portions 19A have the same potential, and the plurality of second electrode portions 20A have the same potential.

It is to be noted that the surfaces of the plurality of first electrode portions 19A, the second electrode portions 20A and the wall portion 26 opposite to the other jaw 11 are integrally formed as the tissue pressing portion 27 in the relatively dull shape as with the embodiment 1, though not shown.

The other constructions are the same as those of the embodiment 1.

In the so constructed forceps of the variation 2, the plurality of first electrode portions 19A and the plurality of second electrode portions 20A are fixed to the insulating member 25 while changing the arrangement positions alternately in the longitudinal direction (axial direction of the forceps 2) of the forceps 2, and in the direction orthogonal to the longitudinal direction of the forceps 2 (the direction orthogonal to the axial direction of the forceps 2), the respective first electrode portions 19A and the second electrode portions 20A are arranged opposing to each other side by side.

Therefore, at coagulation, incision treatments, the high-frequency current flows between the adjoining plurality of the first electrode portions 19A and the plurality of second electrode portions 20A, respectively. In this case, the high-frequency current flows not only between the opposing first electrode portions 19A and the second electrode portions 20A but also between the first electrode portion 19 and the second electrode portion 20A adjoining in the longitudinal direction of the forceps 2 (axial direction of the forceps 2).

That is, in the variation 2, an area of the living tissue 100 where the high-frequency current flows is larger than that of the embodiment 1. By this, it becomes possible to facilitate coagulation and incision of the living tissue 100.

The other actions are the same as those of the embodiment 1.

Therefore, according to the variation 2, since coagulation incision and coagulation treatment performance can be improved in addition to the same effects as those in the embodiment 1, great contribution is made to reduction of time for surgery.

(Variation 3)

Figure 8:
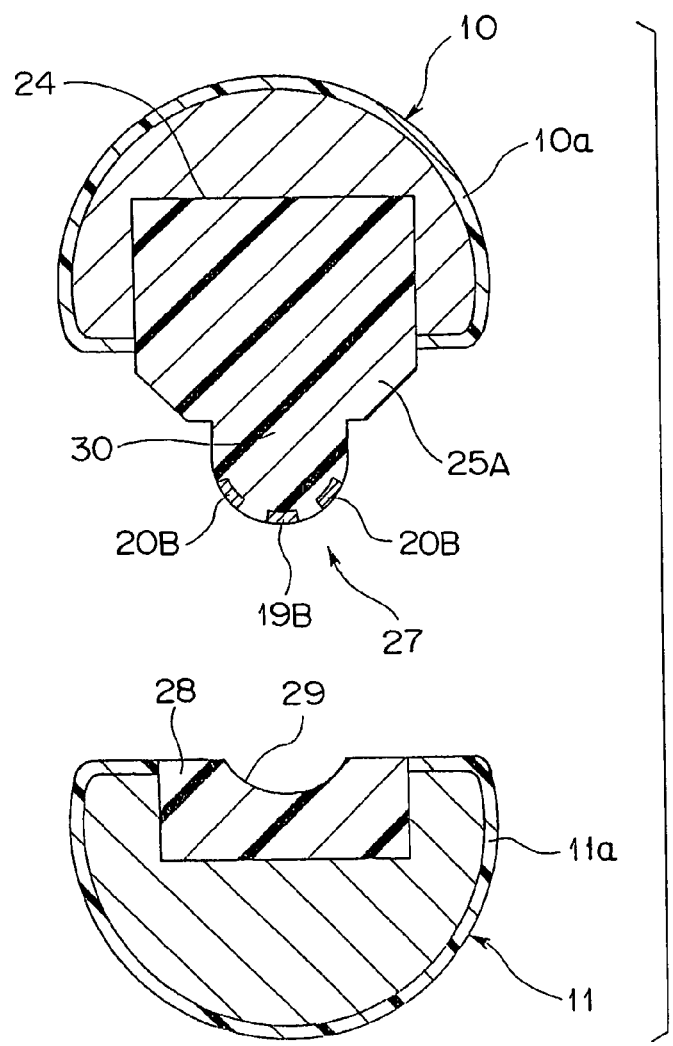
FIG. 8 is a sectional view of a treatment portion showing a variation 3 of the treatment portion in the embodiment 1.

FIG. 8 is a sectional view of a treatment portion showing a variation 3 of the treatment portion in the embodiment 1.

The treatment portion 14 of the embodiment 1 may be constructed as shown in the variation 3 of FIG. 8, for example. That is, as shown in FIG. 8, the treatment portion 14 of the variation 3 comprises a first electrode portion 19B and two electrode portions 20B with different shapes in place of the first electrode portion 19 and the second electrode portion 20 of the embodiment 1 and an insulating member 25A with a different shape in place of the insulating member 25 of the embodiment 1.

Specifically, the insulating member 25A formed using an electrically insulating material is fixed to the recess portion 24 of the jaw 10. At this insulating member 25A, a projection portion 30 projecting toward the other jaw 11 is formed.

In the vicinity of the center of this projection portion 30, the first electrode portion 19B is fixed, and to the both sides of this first electrode portion 19B, the two second electrode portions 20B, 20B are fixed in the state electrically insulated from the first electrode portion 19B.

Also, the first electrode portion 19B and the two second electrode portions 20B, 20B are arranged along the curved shape in the longitudinal direction of the jaw 10 as in the embodiment 1. And the two second electrode portions 20B, 20B have the same potential.

It is to be noted that the surfaces of the first electrode portion 19B, the two second electrode portions 20B, 20B and the projection portion 30 opposite to the other jaw 11 are integrally formed as the tissue pressing portion 27 in the relatively dull shape as in the embodiment 1.

In the variation 3, the first electrode portion 19B and the two second electrode portions 20B, 20B are formed as thin print-type various electrode portions, respectively, and moreover, it may be so constructed that these various electrode portions are applied to a recess groove formed on the outer surface of the projection portion 30 of the insulating member 25A.

The other constructions are the same as those of the embodiment 1.

In the so constructed forceps 2 of the variation 3, the first electrode portion 19B is fixed to the vicinity of the center of the projection portion 30, and at the both sides of this first electrode portion 19B, the two second electrode portions 20B, 20B are fixed in the state electrically insulated from the first electrode portion 19B. And the first electrode portion 19B and the second electrode portions 20B, 20B are arranged along the curved shape in the longitudinal direction of the jaw 10.

Therefore, at coagulation, incision treatments, the high-frequency current flows between the first electrode portion 19B and the two second electrode portions 20B, 20B, respectively.

That is, in the variation 3, too, it is possible to coagulate and incise the living tissue 100 by acting substantially the same as in the embodiment 1.

The other actions are the same as those of the embodiment 1.

Therefore, according to the variation 3, the first electrode portion 19B and the two second electrode portions 20B, 20B can be made smaller than those in the embodiment 1 in addition to the same effects as in the embodiment 1, and moreover, the insulating member 25A can be formed as a main body, whereby costs can be reduced.

(Variation 4)

Figure 9:
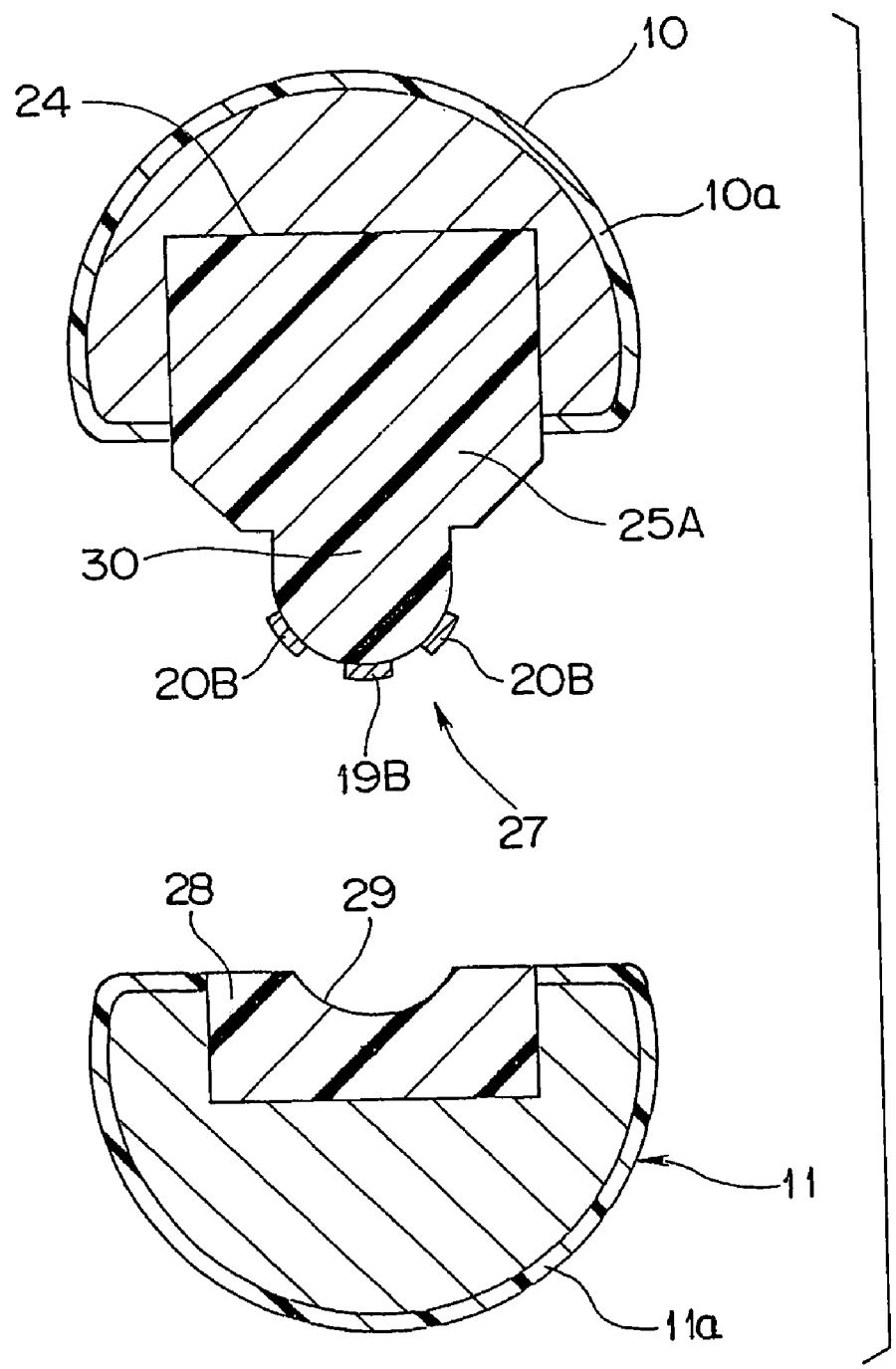
FIG. 9 is a sectional view of a treatment portion showing a variation 4 of the treatment portion in the embodiment 1.

FIG. 9 is a sectional view of a treatment portion showing a variation 4 of the treatment portion in the embodiment 1.

The treatment portion 14 of the embodiment 1 may be constructed as shown in the variation 4 of FIG. 9, for example. That is, as shown in FIG. 9, the treatment portion 14 of the variation 4 comprises the same components as those in the above mentioned variation 3 shown in the FIG. 8, except that the first electrode portion 19B and the two second electrode portions 20B are applied to the outer circumferential surface on the jaw 11 side of the projection portion 30.

That is, the first electrode portion 19B and the two second electrode portions 20B, 20B are formed as thin print-type various electrode portions, respectively, and moreover, these various electrode portions are applied to predetermined positions of the outer surface of the projection portion 30 of the insulating member 25A.

The other constructions are the same as those of the embodiment 3.

Therefore, according to the variation 4, the same effects as those of the variation 3 can be obtained.

(Variation 5)

Figure 10:
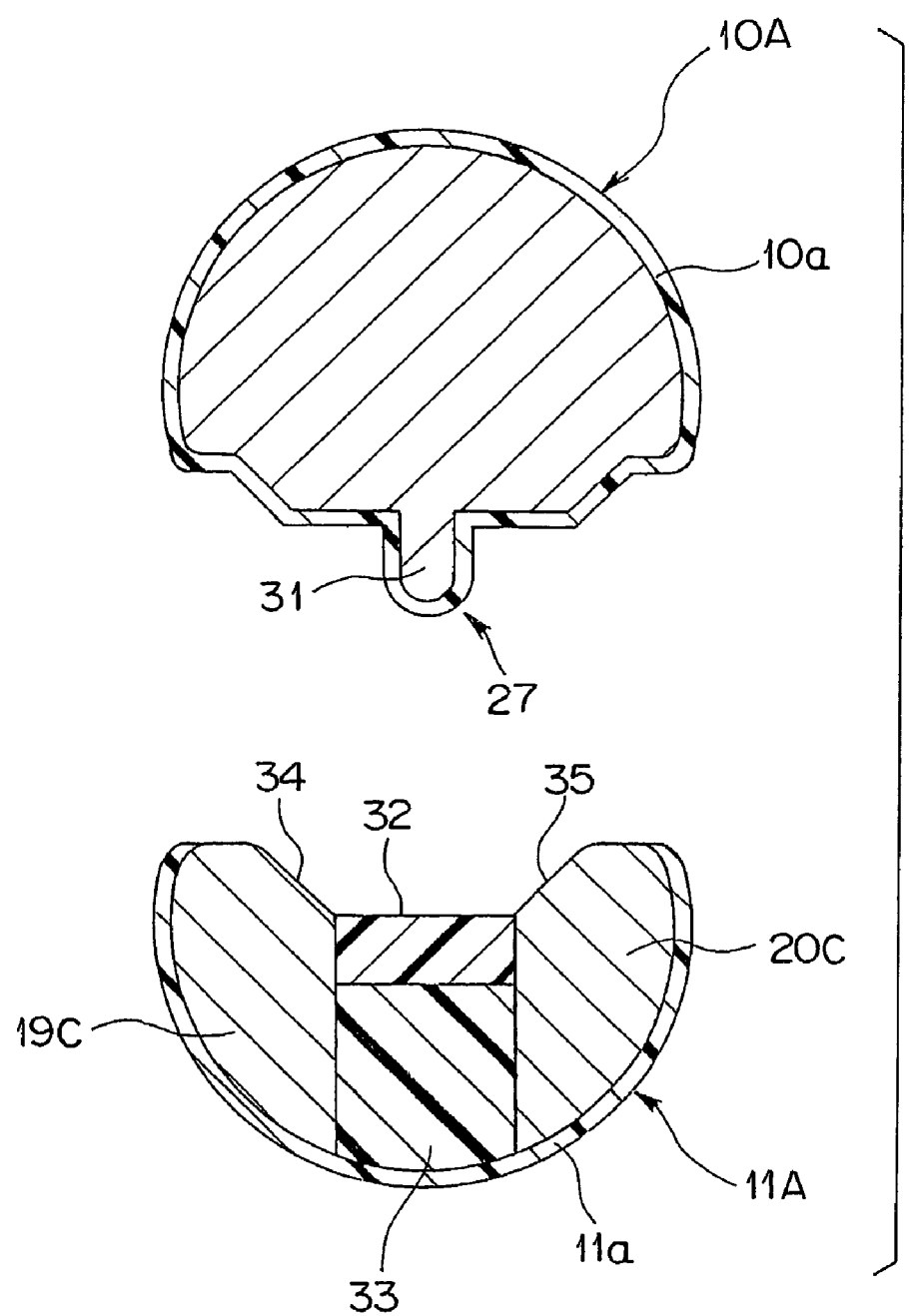
FIG. 10 is a sectional view of a treatment portion showing a variation 5 of the treatment portion in the embodiment 1.

FIG. 10 is a sectional view of a treatment portion showing a variation 5 of the treatment portion in the embodiment 1.

The treatment portion 14 of the embodiment 1 may be constructed as shown in the variation 5 of FIG. 10, for example. That is, as shown in FIG. 10, the treatment portion 14 comprises a pair of jaws 10A, 11A with different wiring of the lead wires 20, 21 and construction of the first, the second electrode portions 19, 20 in place of the pair of jaws 10, 11 in the embodiment 1.

Specifically, as shown in FIG. 10, at the jaw 11A constituting the treatment portion 14, a first electrode portion 19C and a second electrode portion 20C, which will be described later, are provided. And at the jaw 11A, a receiving member 32 is provided at a position opposite to the tissue pressing portion 27 of the jaw 10A, which will be described later.

Moreover, inside a part of the forceps constituting portion 13 (jaw 11A) and the forceps constituting portion 12, two lead wires 21, 22 electrically connected to the first electrode portion 19C and the second electrode portion 20C, respectively, are disposed.

These lead wires 21, 22 extend from the jaw 11A, which is a part of the forceps constituting portion 13 to the handle portion 8 through the fulcrum pin 15, the inside of the forceps constituting portion 12, for example, and is electrically connected to the power supply device 3 from the cord connection portion 23 at the rear end side of the ring 16 through the connection portion 4 as in the embodiment 1.

It is to be noted that by disposing the lead wires 21, 22 inside the forceps constituting portion 13 and by providing the cord connection portion 23 at the rear end side of the forceps constituting portion 13, the lead wires 21, 22 may be constructed to be electrically connected to the power supply device 3 through the connection cord 4.

The surface of the jaw 10A opposite to the other jaw 11A forms the tissue pressing portion 27 having a projection portion 31 in the relatively dull shape. The jaw 10A is formed using a metal material such as stainless, and its outer surface is covered and constructed by the insulating member 10a formed of an electrically insulating material (polytetrafluoroethylene (PTFE) or alumina) as shown in FIG. 10.

Also, the surface of the jaw 11A opposite to the other jaw 10A is formed in the shape with a recessed center portion. And in the jaw 11A, the receiving member 32 is provided at a position opposite to the tissue pressing portion 27 of the jaw 10A. This receiving member 32 is formed using a resin material such as polytetrafluoroethylene (PTFE), silicone rubber or the like with favorable electrical insulation and high heat resistance, as in the embodiment 1. Below this receiving member 32, an insulating member 33, which will be described later, is provided.

At the both sides of the receiving member 32 of the jaw 11A, the first electrode portion 19C and the second electrode portion 20C are provided holding the insulating member 33 with electrical insulation between them. That is, the first electrode portion 19C and the second electrode portion 20C are electrically insulated by the receiving member 32 and the insulating member 33.

The first electrode portion 19C and the second electrode portion 20C are formed using a metal material such as stainless, and the outer surfaces are covered and constructed by an insulating member 11a formed of an electrically insulating material (polytetrafluoroethylene (PTFE) or alumina, for example) except action surfaces 34, 35 opposite to the jaw 10A as shown in FIG. 10.

In the so constructed forceps 2 of the variation 5, at coagulation, incision treatments, the living tissue 100 is gripped between the jaw 10A and the jaw 11A and gripped in the strongly compressed state between the tissue pressing member 27 and the receiving member 32.

After that, as with the embodiment 1, by selectively operating the first operation pedal 6, the second operation pedal 7 of the foot switch 5 by the operator, coagulation, incision treatments of the living tissue 100 is started.

In this case, in the variation 5, at both sides of the receiving member 32 of the jaw 11A, the first electrode portion 19C and the second electrode portion 20C are provided holding the insulating member 33 with electrical insulation between them. Therefore, the high-frequency current flows between the action surfaces 34, 35 of the two first electrode 19C, the second electrode portion 20C from the power supply device 3 through the connection cord 4, the cord connection portion 23 and the lead wires 21, 22.

By this, the high-frequency current flows through the gripped living tissue 100 in an area larger than that in the embodiment 1, and Joule heat is generated locally. And by this Joule heat and the compression force between the tissue pressing portion 27 and the receiving member 32, coagulation, incision or strong coagulation of the living tissue 100 can be performed in a short time. In this case, incision of the living tissue 100 is performed in the vicinity of the center of the tissue pressing portion 27.

The other actions are the same as those of the embodiment 1.

Therefore, according to the variation 5, even if the first electrode, the second electrode portions 19C, 20C are provided at the jaw 11A at the lower part of the treatment portion 14, the same effects as those of the embodiment 1 and the variation 1 can be obtained.

Embodiment 2

Figure 11:
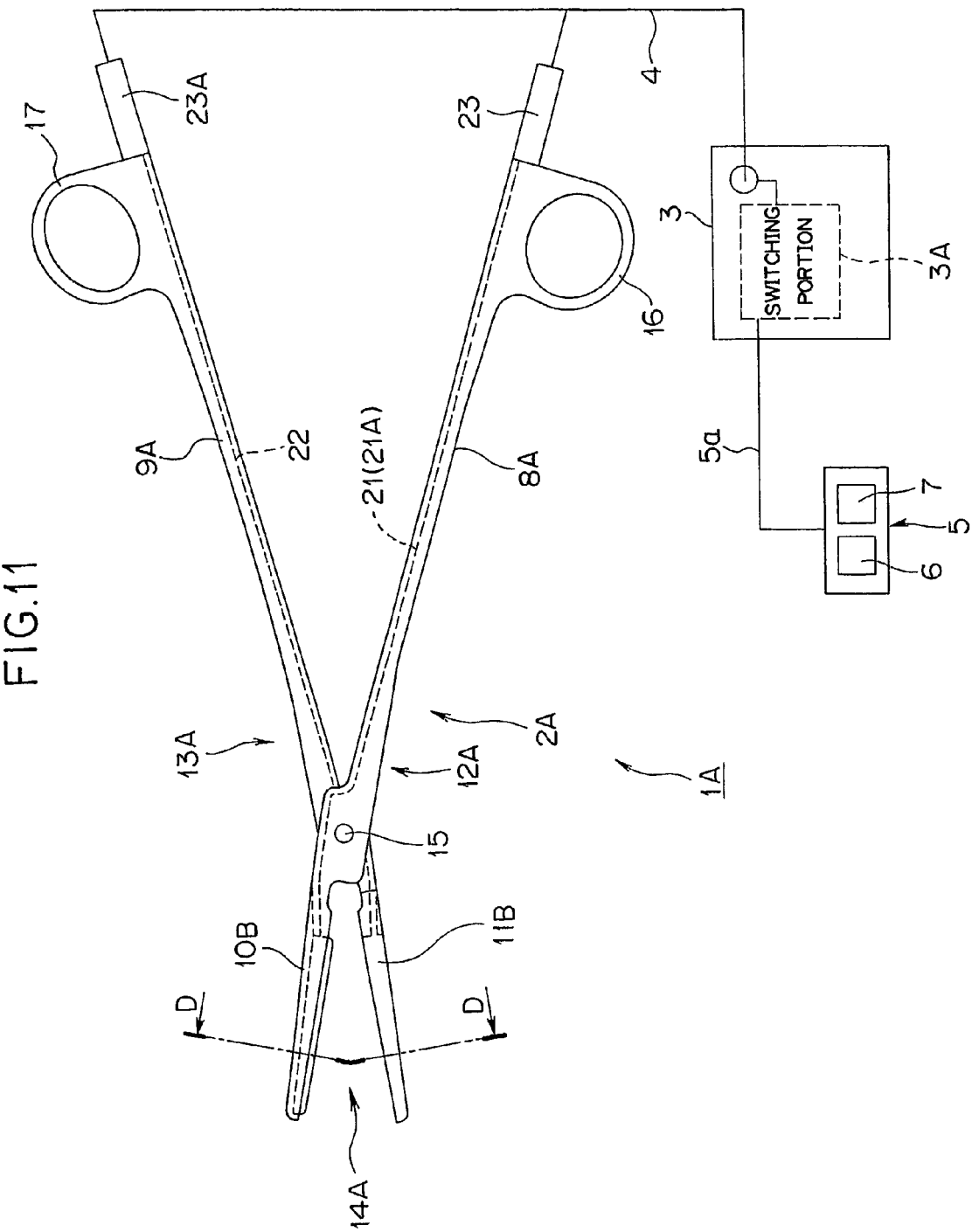
FIG. 11 is a side view showing the entire construction of the treatment device according to an embodiment 2 of the present invention.
Figure 12:
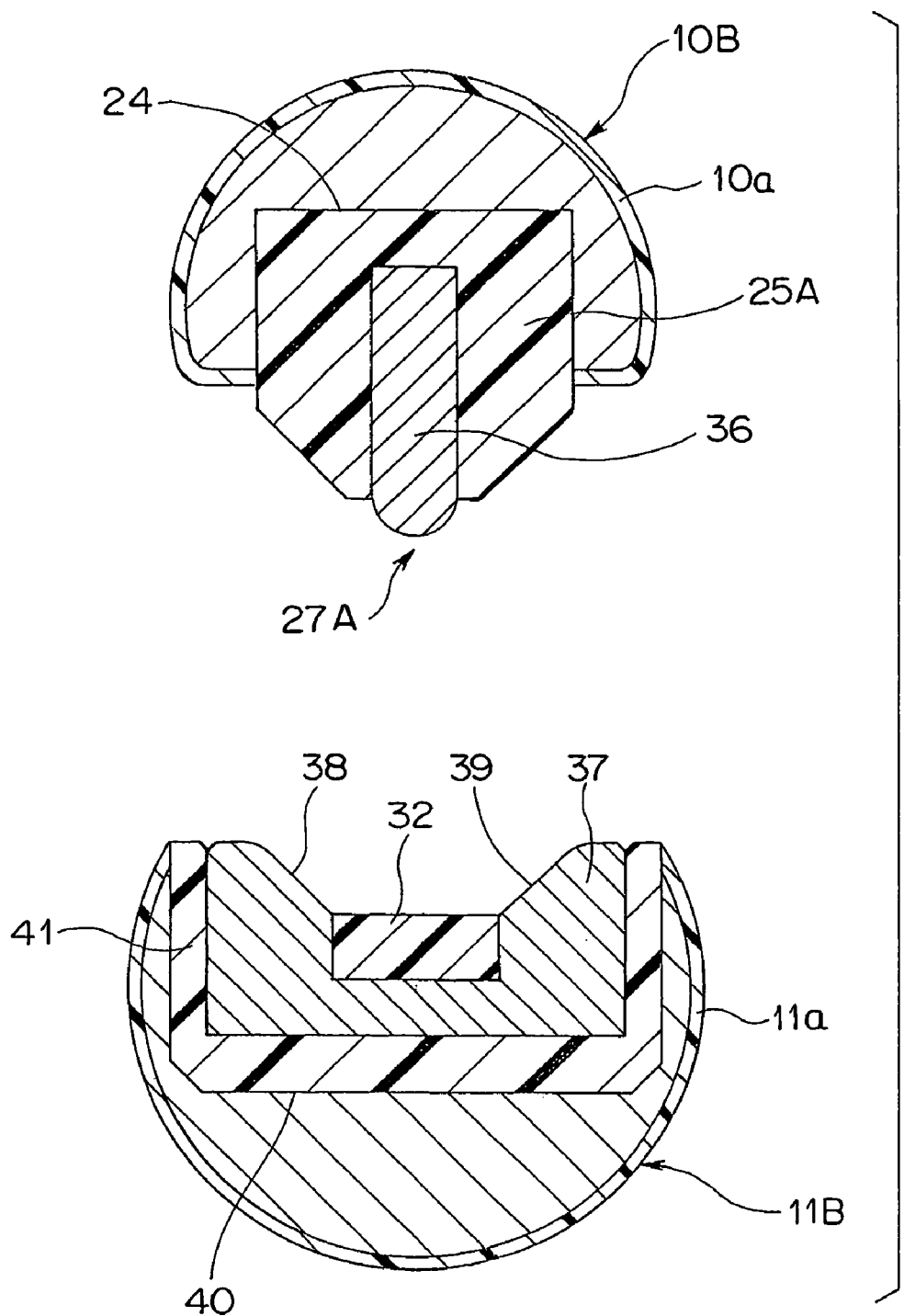
FIG. 12 is a sectional view taken on D-D line in FIG. 11.

FIGS. 11 and 12 relate to an embodiment 2 of the present invention, in which FIG. 11 is a side view showing an entire construction of a treatment device according to the embodiment 2 and FIG. 12 is a sectional view taken on D-D line in FIG. 11. It is to be noted that in FIGS. 11 and 12, the same components as those in the treatment device 1 of the embodiment 1 are given the same reference numerals so as to omit explanation, and only differences will be described.

A treatment device 1A of the embodiment 2 has forceps 2A with construction different from the forceps 2 in the embodiment 1. The entire construction of the forceps 2A is substantially the same as that of the embodiment 1, but it has a pair of jaws 10B, 11B with different construction and forceps constituting portions 12A, 13A.

At the jaw 10B, a first electrode portion 36, which will be described later, is provided, while at the other jaw 11B, a second electrode portion 37, which will be described later, is provided.

The construction of the forceps constituting portions 12A, 13A is substantially the same as that of the embodiment 1, but the lead wire 21 electrically connected to the first electrode portion 36 is disposed inside the forceps constituting portion 12A. Also, inside the forceps constituting portion 13A, the lead wire 22 electrically connected to the second electrode portion 37 is disposed.

The lead wire 21 extends from the jaw 10B to a handle portion 8A and is electrically connected to the power supply device 3 from the cord connection portion 23 on the rear end side of the ring 16 through the connection cord 4.

Also, the lead wire 22 extends from the jaw 11B to a handle portion 9A and is electrically connected to the power supply device 3 from a cord connection portion 23A on the rear end side of the ring 17 through the connection cord 4.

Next, specific construction of a treatment portion 14A of the forceps 2A will be described referring to FIG. 12.

The pair of jaws 10B, 11B constituting the treatment portion 14A of the forceps 2A are formed in the curved tapered shape toward the tip end portion as in the embodiment 1. Also, in the embodiment 2, as shown in FIG. 12, the long-groove state recess portion 24 is formed on the surface of the jaw 10B opposite to the other jaw 11B. To this recess portion 24, the insulating member 25A formed substantially in the U shape using an electrically insulating material is fixed.

To this insulating material 25A, the first electrode portion 36 is fixed while being covered by this insulating member 25A. It is to be noted that this insulating member 25A is formed using the electrically insulating material substantially the same as that of the insulating member 25 of the embodiment 1.

The surface of the first electrode portion 36 (surface portion) opposite to the other jaw 11B is formed in the relatively dull shape, as an arc-shaped tissue pressing portion 27A, for example.

On the other hand, at the other jaw 11B, a long-groove state recess portion 40 is formed at a position opposite to the tissue pressing portion 27A of the other jaw 10B. To this recess portion 40, an insulating member 41 formed in the substantially U shape using an electrically insulating material is fixed. To this insulating member 41, the second electrode portion 37 is fixed while being covered by this insulating member 41. This insulating member 41 is formed using the electrically insulating material substantially the same as that of the insulating member 25A.

The surface of the second electrode portion 37 opposite to the jaw 10B is formed in the shape with the center portion recessed. Also, at this second electrode portion 37, the receiving member 32 is integrally provided at a position opposite to the tissue pressing portion 27A. This receiving member 32 is formed using a resin material such as polytetrafluoroethylene (PTFE), silicon rubber or the like with favorable electrical insulation and high heat resistance.

Also, the second electrode portion 37 has two action surfaces 38, 39 formed in the shape conforming to the shape of the insulating member 25A of the jaw 10B.

The pair of jaws 10B, 11B in this construction are formed using a metal material such as stainless, and their respective outer surfaces are covered and constructed by the insulating members 10a, 11a formed of an electrically insulating material (polytetrafluoroethylene (PTFE) or alumina, for example) as with the embodiment 1 as shown in FIG. 12.

In the embodiment 2 in the above construction, suppose that the first electrode portion 36 is a positive pole, for example, then the second electrode portion 37 is a negative pole, and the high-frequency power flows between the first and the second electrode portions 36, 37.

That is, coagulation, incision treatments of the living tissue 100 can be performed by flowing the high-frequency current between each of the action surfaces 38, 39 of the second electrode portion 37 and the first electrode portion 36 in the state where the living tissue 100 is compressed within a narrow range by the first electrode portion 36 constituting the tissue pressing portion 27A and the receiving member 32.

The other constructions are the same as those of the embodiment 1.

Next, action when treating the living tissue using the treatment device 1A of this embodiment will be described referring to FIG. 12.

The treatment device 1A of the embodiment 2 acts substantially similarly to the embodiment 1. That is, in the forceps 2A of the treatment device 1A of the embodiment 2, at coagulation, incision treatments, the living tissue 100 is gripped between the jaw 10B and the jaw 11B and gripped between the tissue pressing member 27A and the receiving member 32 in the strongly compressed state.

At this time, the living tissue 100 is gripped by the first electrode portion 36 constituting the tissue pressing member 27A and the receiving member 32 in the state compressed in a narrow range.

After that, as with the embodiment 1, by selectively operating the first operation pedal 6, the second operation pedal 7 of the foot switch 5 by the operator, coagulation, incision treatments of the living tissue 100 is started.

In this case, in the embodiment 2, the first electrode portion 36 is provided on the jaw 10B side, while the second electrode portion 37 having the action surfaces 38, 39 is provided on the other jaw 11B side. Therefore, the high-frequency current flows between the first electrode portion 36 and the action surfaces 38, 39 of the second electrode portion 37 from the power supply device 3 through the connection cord 4, the cord connection portions 23, 23A and the lead wires 21, 22.

By this, the high-frequency current flows through the living tissue 100 gripped in the compressed state in a narrow range in an area larger than the embodiment 1, and Joule heat is generated locally. And by this Joule heat and the compression force between the tissue pressing portion 27A and the receiving member 32, coagulation, incision or strong coagulation of the living tissue can be performed in a short time.

The other actions are the same as those of the embodiment 1.

Therefore, according to the embodiment 2, even when the first electrode portion 36 is provided in the jaw 10B and the second electrode portion 37 is provided at the other jaw 11B, substantially the same effects as those of the embodiment 1 can be obtained.

In the embodiment 2, the treatment portion 14A may be constructed as shown in variations 1 to 3, which will be described later.

The variations 1 to 3 of the embodiment 2 will be described referring to FIGS. 13 to 23. The same components as those of the treatment device of the embodiment 2 are given the same reference numerals to omit description and only the differences will be described in FIGS. 13 to 23.

(Variation 1)

Figure 13:
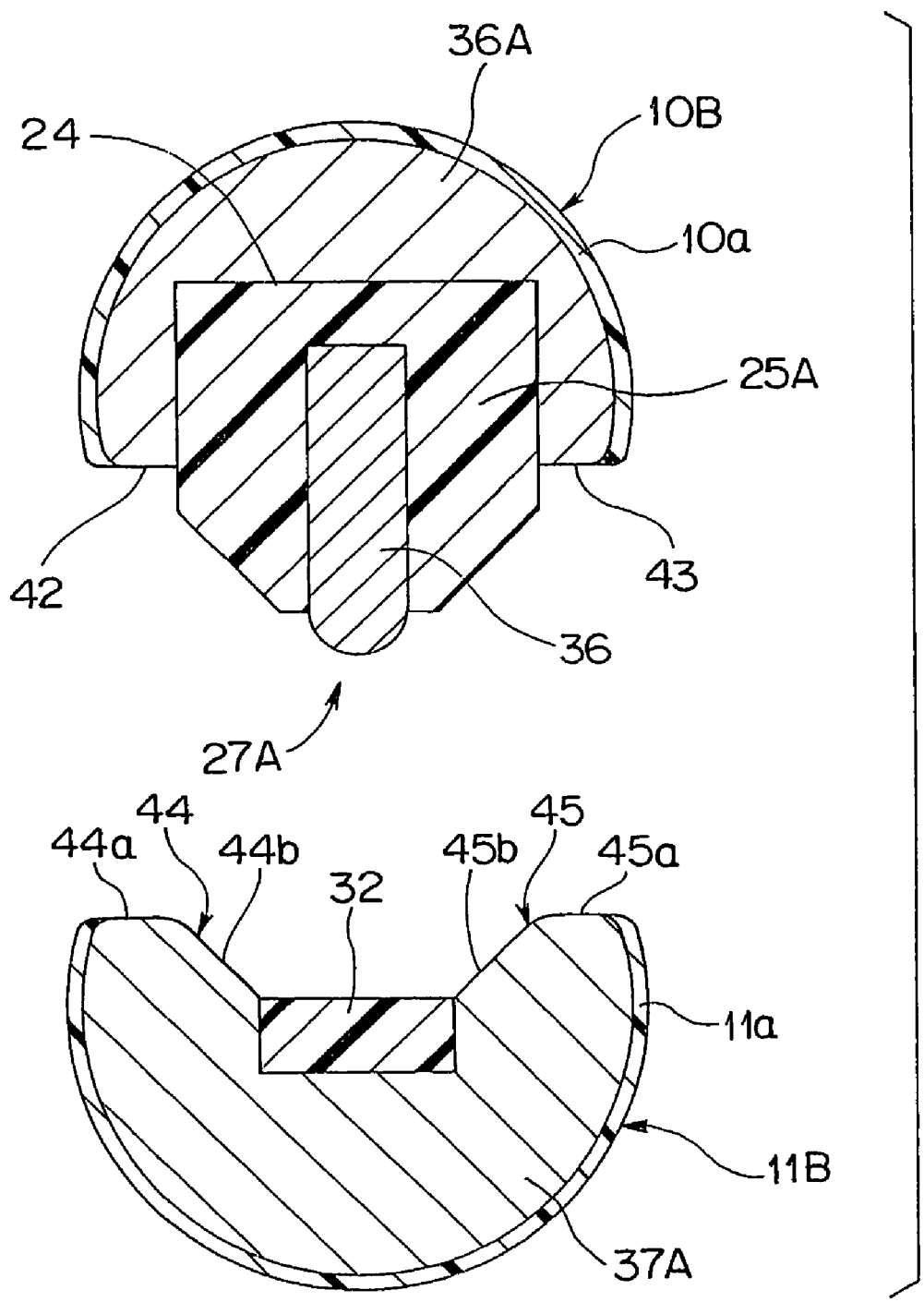
FIG. 13 is a sectional view of a treatment portion showing a variation 1 of the treatment portion in the embodiment 2.
Figure 15:
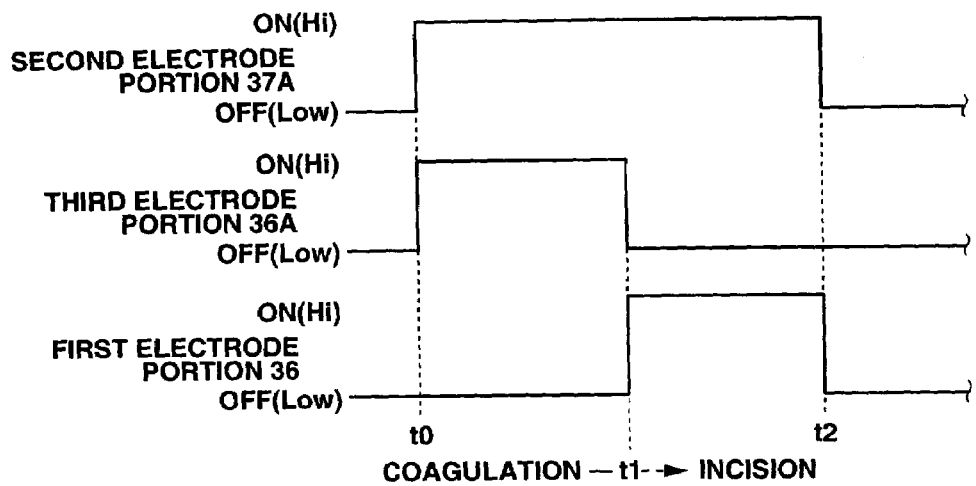
FIG. 15 is a timing chart showing an operating state when switching control of the high-frequency current is performed by the switching portion in FIG. 14.
Figure 14:
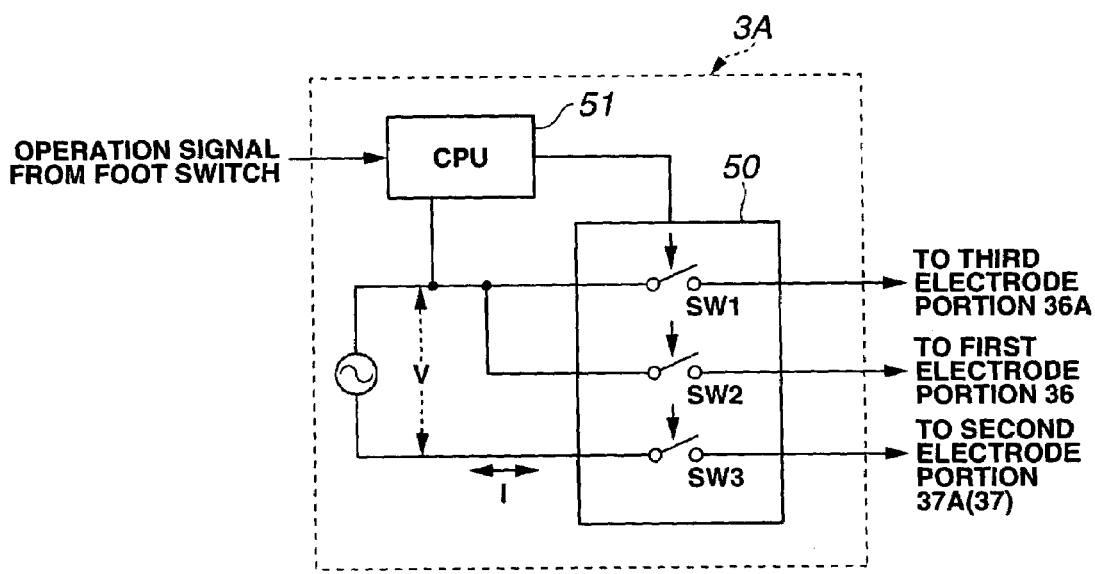
FIG. 14 is a circuit diagram showing a specific configuration of a switching portion for switching a high-frequency current flowing through each electrode portion of the treatment portion.
Figure 16:
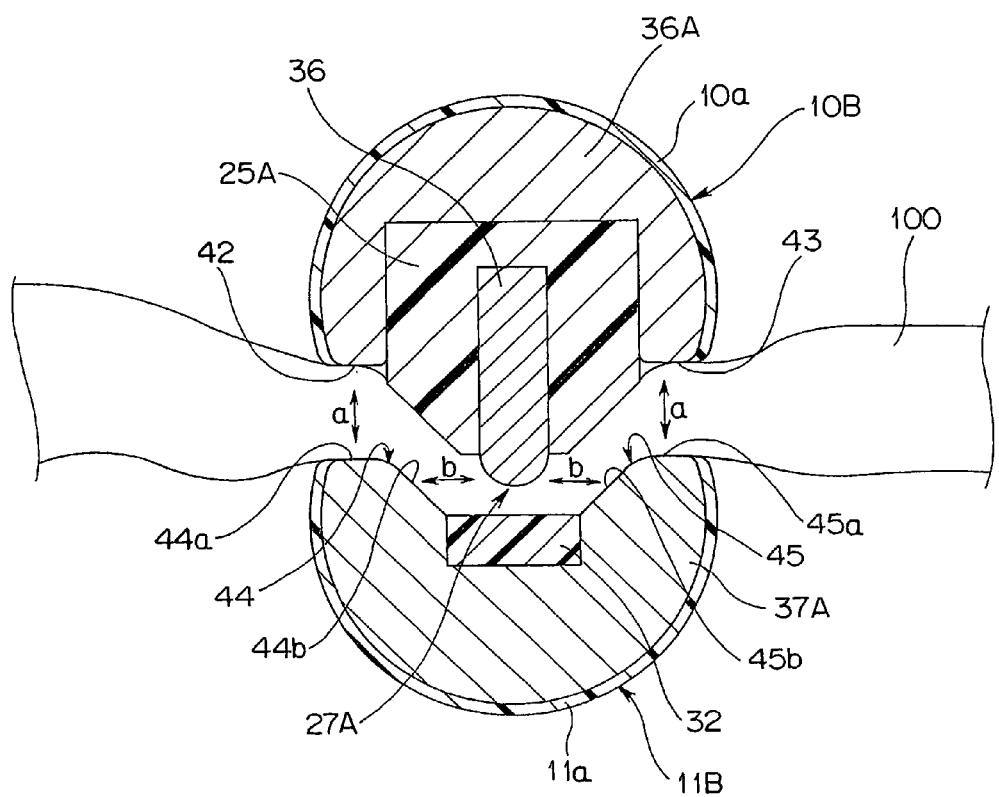
FIG. 16 is an explanatory view for explaining a treatment of a living tissue by the treatment portion of the variation 1 in the embodiment 2.
Figure 17:
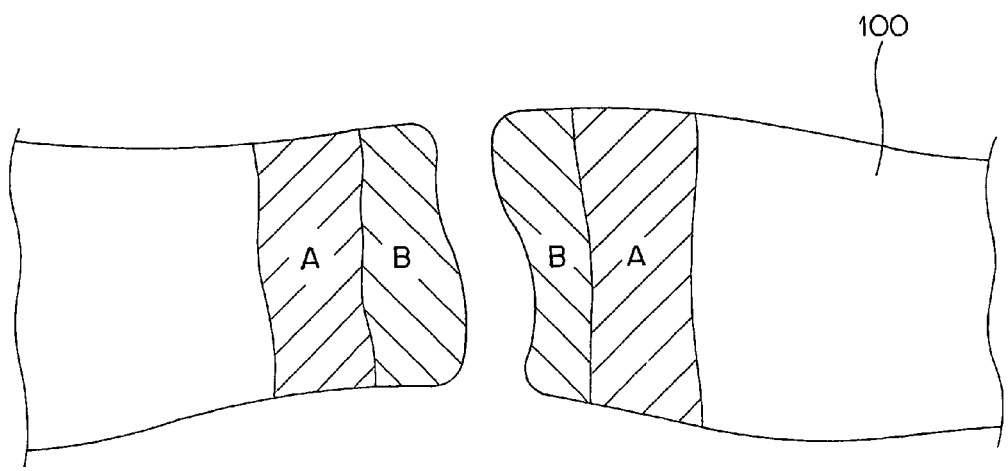
FIG. 17 is a schematic diagram of a living tissue treated by the treatment portion of the variation 1 in the embodiment 2.

FIGS. 13 to 17 show a variation 1 of the treatment portion in the embodiment 2, in which FIG. 13 is a sectional view of the treatment portion of the variation 1, FIG. 14 is a circuit diagram showing specific construction of a switching portion for switching the high-frequency current flowing to each of the electrode portions of the treatment portion, FIG. 15 is a timing chart showing an operating state at switching control of the high-frequency current by the switching portion of FIG. 14, FIG. 16 is an explanatory view for explaining treatment of the living tissue by the treatment portion of the variation 1, and FIG. 17 is a schematic diagram of the living tissue treated by the treatment portion of the variation 1.

The treatment portion 14A of the embodiment 2 may be constructed as shown in the variation 1 of FIG. 13, for example. That is, as shown in FIG. 13, in the treatment portion 14A, the construction of the respective electrode portions (the first electrode portion 36 and the second electrode portion 37) provided at the jaws 10B, 11B constituting this treatment portion 14A is different.

When the construction of the treatment portion 14A is described specifically, as shown in FIG. 13, the long-groove state recess portion 24 is formed on the surface of the jaw 10B opposite to the other jaw 11B as in the embodiment 2. To this recess portion 24, the insulating member 25A formed substantially in the U shape using an electrically insulating material is fixed.

To this insulating member 25A, the first electrode portion 36 is fixed while being covered by this insulating member 25A. Also, the surface (surface portion) of the first electrode portion 36 opposite to the other jaw 11B is formed in the relatively dull shape, as an arc-shaped tissue pressing portion 27A, for example.

In the variation 1, the jaw 10B is formed using a metal material such as stainless as in the embodiment 2, and this jaw 10B itself is constituted as a third electrode portion 36A, which will be described later. Moreover, the outer surface of this third electrode portion 36A is covered and constructed by the insulating member 10a formed of an electrically insulating material (polytetrafluoroethylene (PTFE) or alumina, for example) as with the embodiment 2 as shown in FIG. 13.

On the jaw 11B side of the third electrode portion 36A of the jaw 10B, action surfaces 42, 43 of the third electrode portion 36A not covered by the insulating member 10a are formed.

On the other hand, the surface of the other jaw 11B opposite to the tissue pressing portion 27A of the jaw 10B is formed in the shape with the center portion recessed. Also, at the jaw 11B, the receiving member 32 is integrally provided at a position opposite to the tissue pressing portion 27A. This receiving member 32 is formed using a resin material such as polytetrafluoroehylene (PTFE), silicon rubber or the like with favorable electrical insulation and high heat resistance.

The jaw 11B is formed using a metal material such as stainless as with the embodiment 2, and this jaw 11B itself is constituted as the second electrode portion 37A. Also, the outer surface of this third electrode portion 36A is covered and constructed by an insulating member 11a formed of an electrically insulating material (polytetrafluoroethylene (PTFE) or alumina, for example) as with the embodiment 2 as shown in FIG. 13.

The second electrode portion 37A is formed in the shape conforming to the shape of the insulating member 25A of the jaw 10B and the third electrode portion 36A (respective action surfaces 42, 43) and has two action surfaces 44, 45 not covered by the insulating member 11a.

These two action surfaces 44, 45 have action portions 44a, 45a formed at positions opposite to the action surfaces 42, 43 of the third electrode portion 36A, respectively, and action portions 44b, 45b arranged between these action portions 44a, 45a and the receiving member 32 and formed at positions opposite to the insulating member 25A.

The construction of the forceps constituting portions 12A, 13A is substantially the same as that of the embodiment 2, but the lead wire 21 electrically connected to the first electrode portion 36 is disposed in the forceps constituting portion 12A. Moreover, in the variation 1, a lead wire 21A electrically connected to the jaw 10B, that is, the third electrode portion 36A is disposed inside the forceps constituting portion 12A.

Also, in the forceps constituting portion 13A, the lead wire 22 electrically connected to the jaw 11B, that is, the second electrode portion 37A is disposed.

The lead wires 21, 21A extend from the jaw 10B to the handle portion 8A and are electrically connected to the power supply device 3 from the cord connection portion 23 at the rear end side of the ring 16 through the connection cord 4.

The lead wire 22 extends from the jaw 11B to the handle portion 9A and is electrically connected to the power supply device 3 from the cord connection portion 23A at the rear end side of the ring 17 through the connection cord 4.

In the variation 1, in order to control supply of the high-frequency current to the above constructed forceps 2A, a switching portion 3A (See FIG. 11) is provided as switching means for switching the high-frequency current flowing to the respective electrode portions (first, second and third electrode portions 36, 37A, 36A) of the treatment portion 14A.

This switching portion 3A has a switch 50 having three SW1, 2, 3 electrically connected to a high-frequency power source and the respective electrode portions (first, second and third electrode portions 36, 37A, 36A) of the jaws 10B, 11B for turning on/off supply of the high-frequency current from the high-frequency power source and a CPU 51 as control means for performing switching control of this switch 50 based on an operation signal from the foot switch 5 as shown in FIG. 14.

The CPU 51 controls switching of the switch 50 based on the operation signal from the foot switch 5. In the variation 1, by turning on the first operation pedal 6 by the operator, the foot switch 5 supplies an operation signal indicating instruction of coagulation, incision automatic mode execution to the CPU 51 or by turning on the second operation pedal 7, it supplies an operation signal indicating instruction of the coagulation mode execution to the CPU 51.

For example, when the operation signal indicates instruction of coagulation, incision automatic mode execution, the CPU 51 control to turn on the SW1 and the SW3 of the switch 50 so that the high-frequency current flows through the third electrode portion 36A of the jaw 10B and the second electrode portion 37A of the jaw 11B at a time t0 as shown in FIG. 15. By this, the high-frequency current flows between the third electrode portion 36A of the jaw 10B and the second electrode portion 37A of the jaw 11B (first current path) under a first output condition preset to execute the coagulation mode, for example, so as to perform the coagulation treatment of the living tissue 100.

And the CPU 51 controls to turn off the SW1 of the switch 50 so that the high-frequency current flows to the first electrode portion 36 of the jaw 10B and the second electrode portion 37A of the jaw 11B at a time t1 as shown in FIG. 15 and to turn on the SW2 as well as the SW3 at the same time. By this, the high-frequency current flows to the first electrode portion 36 of the jaw 10B and the second electrode portion 37A of the jaw 11B (second current path) under a second output condition preset to execute the coagulation, incision mode, for example, so as to perform the incision treatment of the living tissue 100.

Also, when the operation signal indicates an instruction to execute the coagulation mode, the CPU 51 controls to turn on the SW1 and the SW3 of the switch 50 so that the high-frequency current flows to the third electrode portion 36A of the jaw 10B and the second electrode portion 37A of the jaw 11B substantially similarly to the above coagulation, incision automatic mode as shown in FIG. 15.

By this, the high-frequency current flows between the third electrode portion 36A of the jaw 10B and the second electrode portion 37A of the jaw 11B under the first output condition preset to execute the coagulation mode, for example, substantially similarly to the coagulation operation when the above coagulation, incision automatic mode is executed so as to perform the coagulation treatment of the living tissue 100.

If, in the above coagulation, incision automatic mode, impedance of the living tissue 100 between the third electrode portion 36A and the second electrode portion 37A is detected when the coagulation mode is executed, for example, and this impedance becomes higher than a predetermined threshold value, the CPU 51 controls to turn off the SW1 of the switch 50 and to turn on the SW3 and the SW2 so as to automatically execute the above coagulation, incision automatic mode.

Specifically, by providing means for detecting a current value I flowing to the switch 50 and an applied voltage value V and supplying them to the CPU 51, though not shown, and by performing determination processing with respect to the predetermined threshold value by the CPU 51 based on the supplied current value I and the voltage value V, it is possible to automatically execute mode switching operation, that is, to perform the coagulation, incision automatic mode.

The other constructions are the same as those of the embodiment 2.

Next, action when the living tissue is treated using the treatment device 1A of the variation 1 will be described referring to FIGS. 13 to 16.

In the forceps 2A of the treatment device 1A of the variation 1, the living tissue 100 is gripped between the jaw 10B and the jaw 11B at the coagulation, incision treatments as with the embodiment 2. At this time, as shown in FIG. 16, the living tissue 100 is gripped in the state strongly compressed between the tissue pressing member 27A and the receiving member 32, and the action surfaces 42, 43 of the third electrode portion 36A and the action surfaces 44, 45 of the second electrode portion 37A.

After that, the operator grips the living tissue 100 and then, operates to selectively turn on the first operation pedal 6, the second operation pedal 7 of the foot switch 5 so as to start the coagulation, and incision treatments.

Here, the power supply device 3 is driven under the first output condition preset to execute the coagulation, incision automatic mode by turning on the first operation pedal 6, while the power supply device 3 is driven under the second output condition preset to execute the coagulation mode by turning on the second operation pedal 7. The first output condition has a first set value required to coagulate the living tissue and a second set value required to incise the living tissue, and this first set value is substantially the same as the second output condition required to execute the above coagulation mode.

Next, more specific action at coagulation and incision in the treatment device of this variation 1 will be described.

Suppose that the operator operates to turn on the first operation pedal 6 of the footswitch 5, for example, to execute the coagulation, incision automatic mode. Then, the power supply device 3 controls to turn on supply of the high-frequency power to the forceps 2A.

Specifically, as shown in FIGS. 14, 15, the CPU 51 of the power supply device 3 controls to turn on the SW1 and the SW3 of the switch 50 so that the high-frequency current with the coagulation waveform (burst wave) flows between the third electrode portion 36A of the jaw 10B and the second electrode portion 37A of the jaw 11B (first current path) at the time t0.

Then, the high-frequency current with the coagulation waveform (burst wave) flows under the first output condition preset to execute the coagulation mode, for example, flows between the third electrode portion 36A of the jaw 10B and the second electrode portion 37A of the jaw 11B.

At this time, the high-frequency current flows through the gripped living tissue 100 through the first current path as shown by an arrow a in FIG. 16. By this, Joule heat is generated locally and intermittently. By this Joule heat and the compression force between the action surfaces 4243 of the third electrode portion 36A and the action surfaces 44, 45 of the second electrode portion 37A, the living tissue 100 is strongly coagulated in the first current path shown by the arrow a in FIG. 16.

Then, the CPU 51 of the power supply device 3 controls to turn off the SW1 of the switch 50 and to turn on the SW3 as well as the SW2 at the same time so that the high-frequency current with the incision waveform (continuous sinusoidal wave) flows between the first electrode portion 36 of the jaw 10B and the second electrode portion 37A of the jaw 11B at the time t1 as shown in FIGS. 14 and 15.

Then, the high-frequency current with the incision waveform (continuous sinusoidal wave) flows between the first electrode portion 36 of the jaw 10B and the second electrode portion 37A of the jaw 11B under the second output condition preset to execute the incision mode, for example.

At this time, the high-frequency current flows through the second current path as shown by an arrow b in FIG. 16. By this, Joule heat is generated locally and continuously. By this Joule heat and the compression force between the tissue pressing portion 27A and the receiving member 32, the living tissue 100 is incised in the vicinity at the center of the tissue pressing portion 27A. Thus, incision can be performed quickly in the state where the living tissue 100 is sufficiently coagulated.

Switching from the first current path to the second current path is automatically controlled by the switching portion 3A (specifically the CPU 51) in the power supply deice 3 shown in FIG. 14 as mentioned above. In this case, in the variation 1, switching from the coagulation mode to the incision mode by the CPU 51 of the switching portion 3A is performed based on an elapsed time from start of output (time from the time t0 to the time t1 in FIG. 15) or the change in impedance in the living tissue 100 as mentioned above, specifically the change in impedance in the first current path.

Also, a schematic diagram of the living tissue when treated in the coagulation, incision automatic mode is shown in FIG. 17. That is, when treated by executing the coagulation, incision automatic mode, as shown in FIG. 17, an area A of the living tissue 100 is a coagulation range by the first current path, while an area B is an incision range by the second current path.

On the other hand, suppose that the operator executes the coagulation mode by controlling to turn on the second operation pedal 7 of the foot switch 5, for example. Then, the power supply device 3 controls to turn on supply of the high-frequency power to the forceps 2A.

Specifically, as with the execution of the coagulation mode in the coagulation, incision automatic mode, the CPU 51 of the power supply device 3 controls to turn on the SW1 and the SW3 of the switch 50 so that the high-frequency current with the coagulation waveform (burst wave) flows between the third electrode portion 36A of the jaw 10B and the second electrode portion 37A of the jaw 11B (first current path) (See FIGS. 14 and 15).

Then, the high-frequency current with the coagulation waveform (burst wave) flows between the third electrode portion 36A of the jaw 10B and the second electrode portion 37A of the jaw 11B under the first output condition preset to execute the coagulation mode, for example.

At this time, the high-frequency current flows through the gripped living tissue 100 through the first current path as shown by the arrow a in FIG. 16. By this, Joule heat is generated locally and intermittently. By this Joule heat and the compression force between the action surfaces 42, 43 of the third electrode portion 36A and the action surfaces 44, 45 of the second electrode portion 37A, the living tissue 100 is strongly coagulated in the first current path shown by the arrow a in FIG. 16. In this case, unlike the case where the first operation pedal 6 is operated to be turned on, that is, since the coagulation, incision automatic mode is not being executed, the high-frequency current with the incision waveform does not flow between the first electrode portion 36 and the second electrode portion 37A. Thus, the living tissue 100s is not incised but stronger coagulation is made possible.

As mentioned above, when the operator selectively operates the first operation pedal 6, the second operation pedal 7 of the foot switch 5, treatment according to the target living tissue can be performed by one type of the forceps 2.

In the variation 1, it may be so constructed and controlled so that the high-frequency current flows in combination of the current paths and the waveforms other than those mentioned above. It may be so constituted, for example, that the second electrode portion 37A and the third electrode portion 36A have the same potential and the high-frequency current with the incision waveform flows between them and the first electrode portion 36.

Therefore, according to the variation 1, the same effects as those of the embodiment 2 can be obtained and moreover, execution of the incision, coagulation execution mode is made possible in which the coagulation mode and the incision mode are automatically switched.

(Variation 2)

Figure 18:
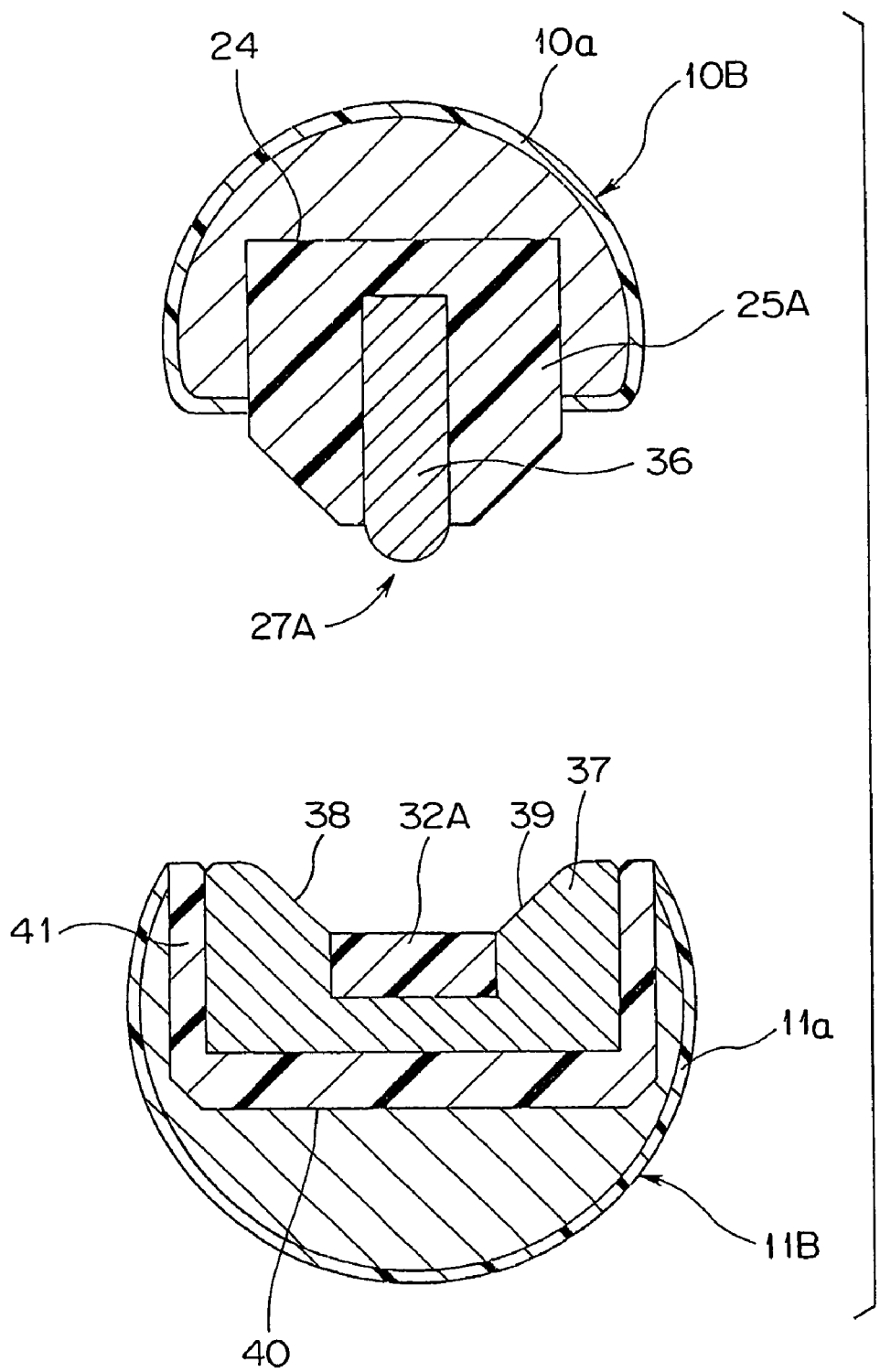
FIG. 18 is a sectional view of the treatment portion showing the variation 2 of the treatment portion in the embodiment 2.
Figure 19:
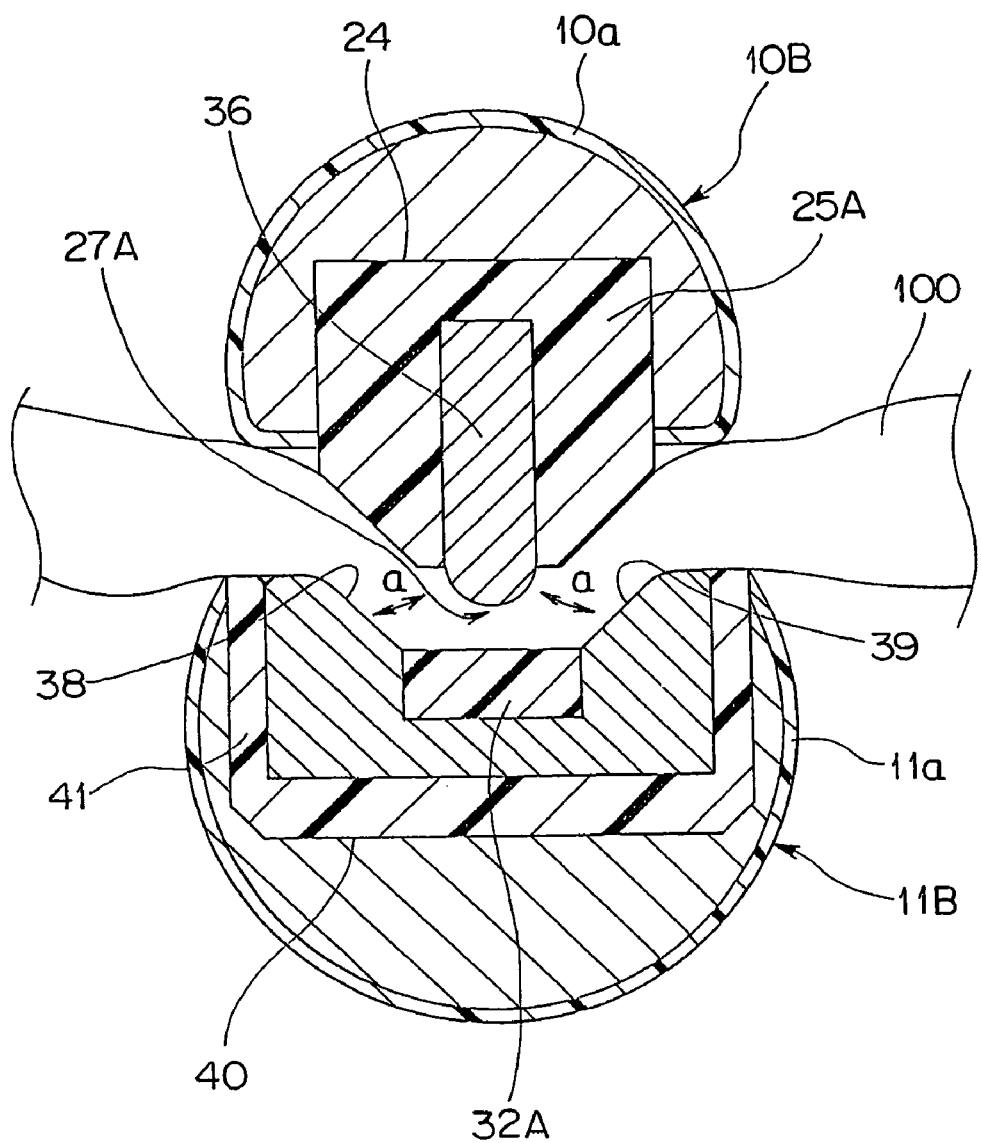
FIG. 19 is an explanatory view showing a state where the living tissue is coagulation/treated to explain a treatment action by the treatment portion in FIG. 18.
Figure 20:
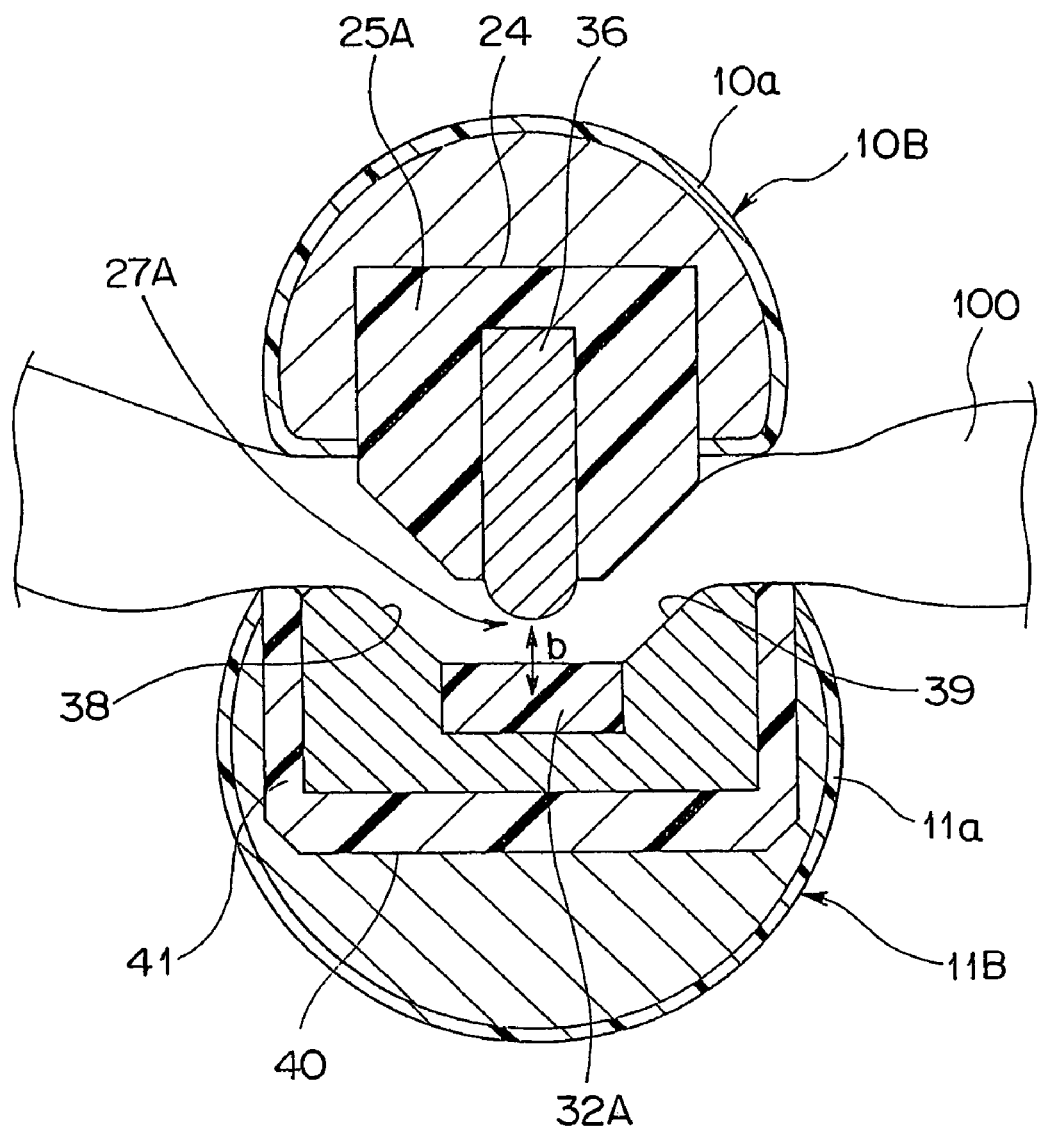
FIG. 20 is an explanatory view showing a state where the living tissue is incised/treated from the state shown in FIG. 19.
Figure 21:
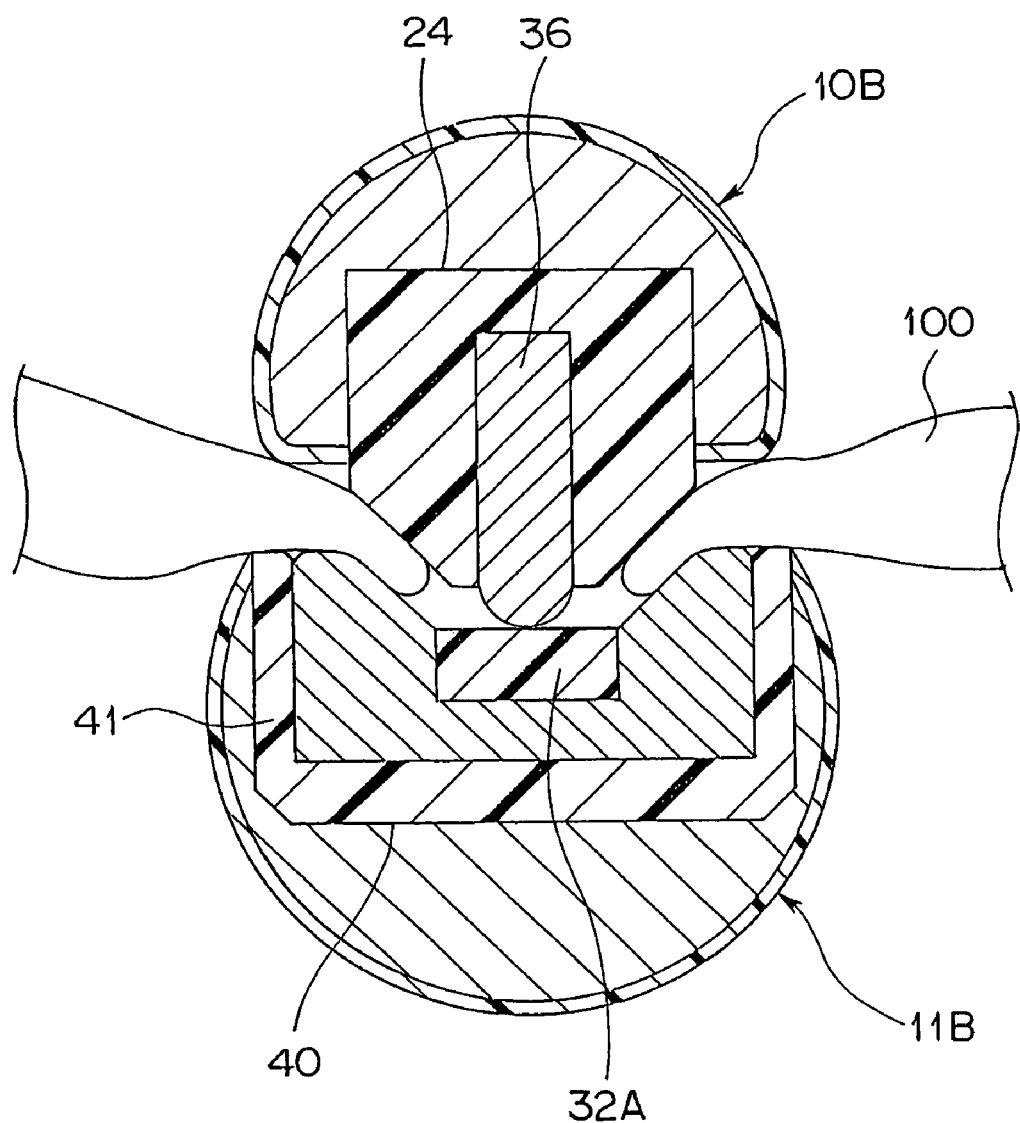
FIG. 21 is an explanatory view showing a state where the living tissue has been incised/treated from the state shown in FIG. 20.
Figure 22:
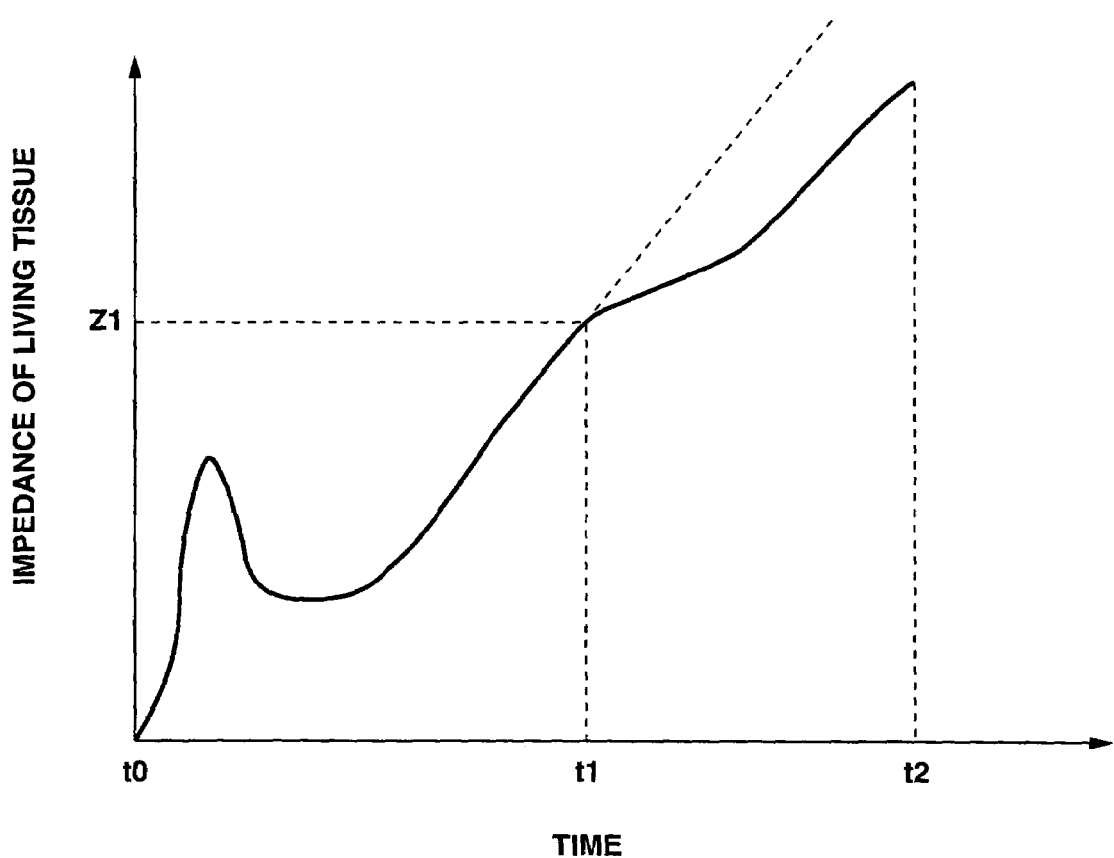
FIG. 22 is a graph showing impedance change of the living tissue at treatment.

FIGS. 18 to 22 show a variation 2 of the treatment portion in the embodiment 2, in which FIG. 18 is a sectional view of a treatment portion of the variation 2, FIGS. 19 to 21 are explanatory views for explaining treatment action by the treatment portion in FIG. 18, in which FIG. 19 shows a state where a living tissue is coagulated/treated, FIG. 20 shows a state where the living tissue is incised/treated from the state shown in FIG. 19, and FIG. 21 shows a state where the living tissue is incised/treated from the state shown in FIG. 20, respectively. Also, FIG. 22 is a graph showing impedance change of the living tissue at treatment.

The treatment portion 14A of the embodiment 2 may be constructed as shown in the variation 2 of FIG. 18, for example. That is, as shown in FIG. 18, the jaw 11B constituting the treatment portion 14A comprises a receiving member 32A with a different material in place of the receiving member 32 in the embodiment 2.

The construction of this receiving member 32A is substantially the same as that of the embodiment 2, but this receiving member 32A is formed of a conductive resin material or an elastic material having a relatively high resistance rate, for example. For example, the receiving member 32A is formed of conductive silicon rubber, conductive polytetrafluoroehylene (PTFE) or the like. Also, the electric resistance of this receiving member 32A is approximately 500 Ω to 1000 Ω, for example.

In the variation 2, the power supply device 3 has the switching portion 3A (See FIG. 14) as with the variation 1. In this case, the SW2 shown in FIG. 14 is electrically connected to the first electrode portion 36, while the SW3 is electrically connected to the second electrode portion 37.

The CPU 51 of this switching portion 3A detects impedance of the living tissue 100 between the first electrode portion 36 and the second electrode portion 37 at output so as to control on/off of the SW2, the SW3 so that the high-frequency current flows or the high-frequency current does not flow between the first electrode portion 36 and the second electrode portion 37A based on the comparison result between this impedance and a predetermined threshold value (predetermined value Z1), which will be described later. Specifically, the CPU 51 detects the current value I flowing to the switch 50 and calculates the impedance based on this detected current value I and the applied voltage value V of this high-frequency power source.

The other constructions are the same as those of the embodiment 2.

Next, action when the living tissue is treated using the treatment device 1A of the variation 2 will be described referring to FIGS. 14 and 19 to 21.

In the forceps 2A of the treatment device 1A of the variation 2, at coagulation, incision treatments, the living tissue 100 is gripped between the jaw 10B and the jaw 11B as with the embodiment 2. At this time, as shown in FIG. 19, the living tissue 100 is gripped between the tissue pressing member 27A and the receiving member 32A in the strongly compressed state.

After that, the operator grips the living tissue 100 and then, the operator selectively operates to turn on the first operation pedal 6, the second operation pedal 7 of the foot switch 5 so as to start coagulation and incision treatments.

Here, by operating to turn on the first operation pedal 6, the power supply device 3 is driven under the first output condition preset to execute the coagulation, incision mode, while by operating to turn on the second operation pedal 7, the power supply device 3 is driven under the second output condition preset to execute the coagulation mode.

Next, more specific action at coagulation and incision in the treatment device of this variation 2 will be described.

Suppose that the operator operates to turn on the first operation pedal 6 of the foot switch 5, for example, to execute the coagulation, incision mode. Then, the power supply device 3 controls to turn on supply of the high-frequency power to the forceps 2A.

Specifically, the CPU 51 of the power supply device 3 controls to turn on the SWs 2, 3 of the switch 50 so that the high-frequency current (continuous sinusoidal wave) flows between the first electrode portion 36 of the jaw 10B and the second electrode portion 37 of the jaw 11B (first current path) as shown in FIGS. 14 and 19.

Then, the high-frequency current with incision waveform (continuous sinusoidal wave) flows between the first electrode portion 36 of the jaw 10B and the second electrode portion 37 of the jaw 11B under the first output condition preset to execute the coagulation, incision mode, for example.

At this time, the high-frequency current flows through the gripped living tissue 100 in the first current path as shown by the arrow a in FIG. 19. By this, Joule heat is generated locally and continuously.

The characteristic of impedance change of the living tissue 100 from this time is shown in FIG. 22. That is, as shown in FIG. 22, the impedance of the living tissue 100 has a characteristic of rising once immediately after output start (time t0) and dropping and then, continuing to rise.

And after coagulation (drying) of the living tissue 100 has progressed, the impedance of the living tissue 100 in the first current path reaches a predetermined value Z1. This predetermined value Z1 is substantially equal to the impedance of the receiving member 32A.

Thus, after the impedance of the living tissue 100 in the first current path reaches the predetermined value Z1 (time t1), the high-frequency current with the incision waveform (continuous sinusoidal wave) flows to the second current path (the path through which the high-frequency current flows from the first electrode portion 36 to the second electrode portion 37 through the living tissue 100 and the receiving member 32A) as shown by the arrow b in FIG. 20. By this, in the second current path as shown by the arrow b in FIG. 20, Joule heat is generated locally and continuously.

In this case, the predetermined value Z1 of the impedance in the first current path (that is, the impedance of the receiving member 32A) is set so that the living tissue 100 reaches the coagulation action temperature but not the incision action temperature higher than that. By this, the living tissue 100 is strongly coagulated in the first current path as shown by the arrow a in FIG. 19.

Moreover, in the second current path as shown by the arrow b in FIG. 20, by the Joule heat locally generated close to the center of the tissue pressing portion 27A and the compression force between the tissue pressing portion 27A and the receiving member 32A, the living tissue 100 is incised as shown in FIG. 21 at a time t2 (See FIG. 22). That is, under the first output condition, the living tissue 100 can be incised quickly in the state it is sufficiently coagulated.

If the electrical resistance of the receiving member 32A is low, the first electrode portion 36 and the second electrode portion 37 are short-circuited at a portion where the living tissue 100 is partially cut off, the high-frequency current does not flow to the uncut portion and the living tissue 100 is partially left uncut. However, in the variation 2, since the receiving member 32A has a relatively high electrical resistance, imperfect cutting hardly occurs in the living tissue 100. By this, sure coagulation, incision are made possible.

Also, the CUP 51 of the power supply device 3 controls to flow the high-frequency current under the first output condition even if the impedance of the living tissue 100 exceeds the predetermined value Z1 when the coagulation, incision mode is executed by operation instruction of the first operation pedal 6.

On the other hand, suppose that the operator operates to turn on the second operation pedal 7 of the foot switch 5, for example, to execute the coagulation mode. Then, the power supply device 3 controls to turn on supply of the high-frequency power to the forceps 2A.

Specifically, similarly to the coagulation, incision mode execution, the CPU 51 of the power supply device 3 controls to turn on the SWs2, 3 of the switch 50 so that the high-frequency current with the incision waveform (continuous sinusoidal wave) flows to the first electrode portion 36 of the jaw 10B and the second electrode portion 37 of the jaw 11B (first current path) similarly to the first output condition.

Then, the high-frequency current with the incision waveform (continuous sinusoidal wave) flows between the first electrode portion 36 of the jaw 10B and the second electrode portion 37 of the jaw 11B under the second output condition set similarly to the first output condition, for example.

Then, the impedance of the living tissue 100 in the first current path rises as shown in FIG. 22 similarly to the above and then, reaches the predetermined value Z1.

Then, the CPU 51 of the power supply device 3 compares the detected impedance of the living tissue 100 with the predetermined value Z1 and recognizes that the impedance of the living tissue 100 has reached the predetermined value Z1.

Then, the CPU 51 controls to turn off the SWs 2, 3 of the switch 50 at the time t1 when the impedance of the living tissue 100 is reached this predetermined value Z1. Therefore, the high-frequency current having flown between the first electrode portion 36 of the jaw 10B and the second electrode portion 37 of the jaw 11B (first current path) is shut off.

By this, the living tissue 100 is not incised but strongly coagulated in the first current path as shown by the arrow a in FIG. 19. In the variation 2, such a case was described that when the coagulation, incision mode and the coagulation mode are executed, the high-frequency current with the incision waveform (continuous sinusoidal wave) is made to flow between the first electrode portion 36 and the second electrode portion 37 in the respective modes. However, it is not limited and the high-frequency current with the coagulation waveform (burst wave) may be made to flow. In this case, too, the same effects as the above can be obtained.

Therefore, according to the variation 2, even if the high-frequency current of one output condition is made to flow between the first electrode portion 36 and the second electrode portion 37, the same effects as those of the embodiment 2 can be obtained.

(Variation 3)

Figure 23:
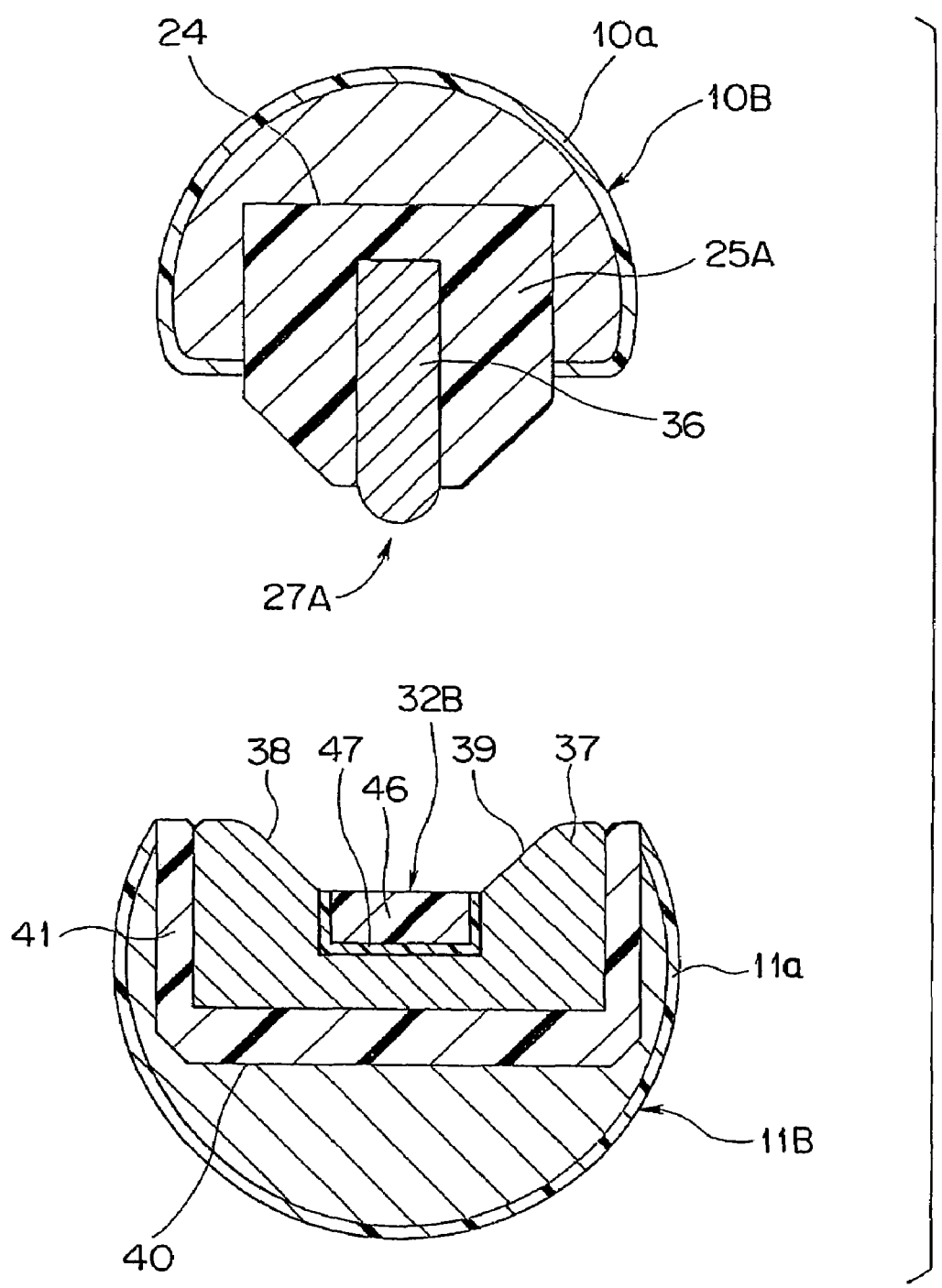
FIG. 23 is a sectional view of the treatment portion showing the variation 3 of the treatment portion in the embodiment 2.

FIG. 23 is a sectional view of a treatment portion showing a variation 3 of the treatment portion in the embodiment 2.

The treatment portion 14A of the embodiment 2 may be constituted as shown in the variation 3 of FIG. 23, for example. That is, as shown in FIG. 23, the treatment portion 14A of the variation 3 comprises the same components as those of the variation 2 shown in the above FIGS. 18 to 21 except a receiving member 32B with the construction different from that of the receiving member 32A.

Specifically, as shown in FIG. 23, the receiving member 32B comprises a conductive resin member 46 having low resistance rate and a semiconductive member 47 provided between the second electrode portion 37 and the resin member 46 and formed substantially in the U shape.

As the material for the resin member 46 and the semiconductive member 47, conductive silicon rubber or conductive polytetrafluoroehylene (PTFE) or the like is used.

Also, the electrical resistance of the resin member 46 is not more than 10 $\Omega$, for example, and the electrical resistance of the semiconductive member 47 is about 500 to 1000 $\Omega$, for example.

In the variation 3, instead of providing the semiconductive member 47, the conductive resin member 46 may be coated with semiconductive thin film coating of about 500 to 1000 $\Omega$, for example.

The other constructions are the same as those of the above variation 2, and the action and effects of the variation 2 are also the same as those of the above variation 2.

Figure 24:
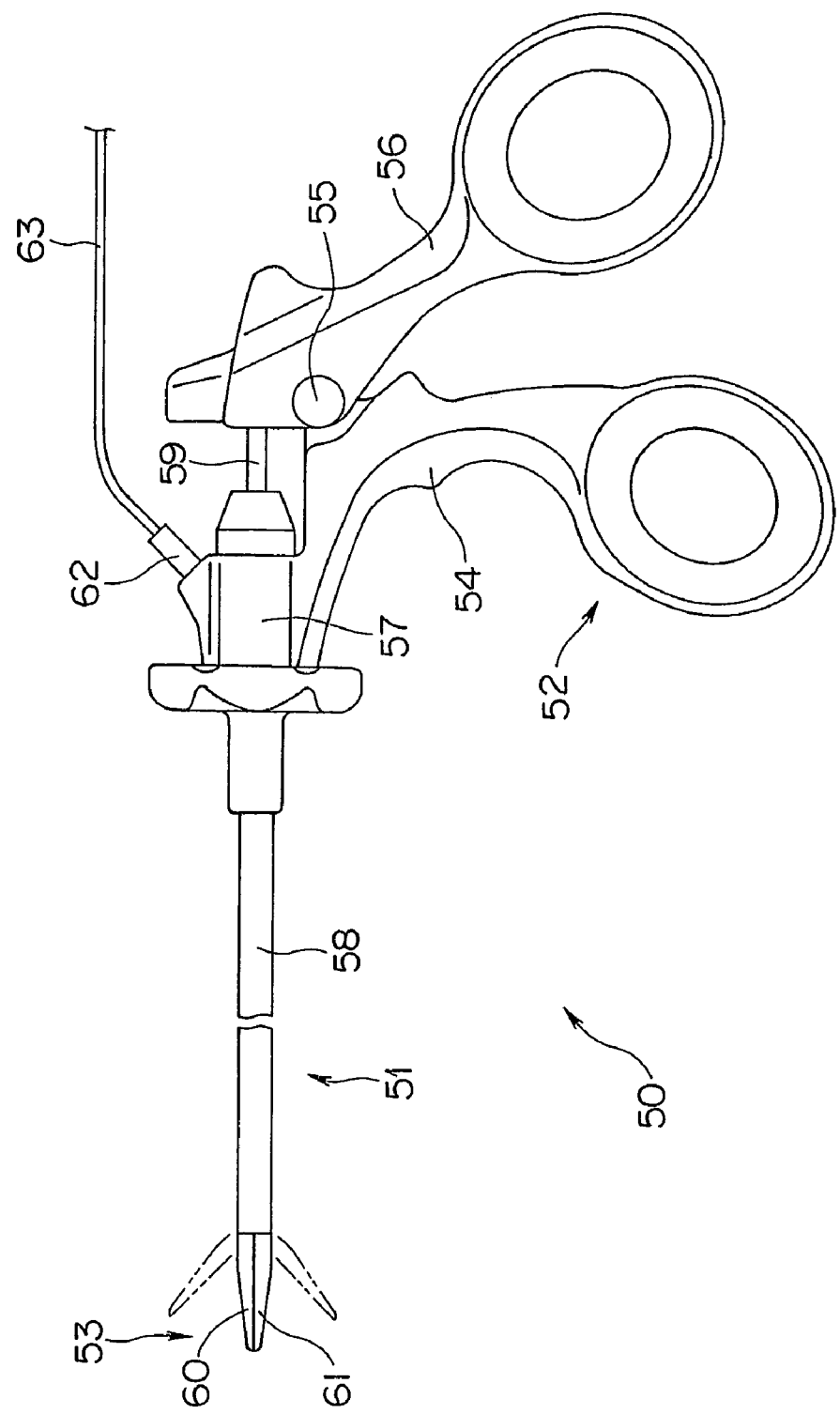
FIG. 24 is a side view showing a construction of forceps suitable for a surgery under endoscope to which the treatment device in the embodiment 1 and the embodiment 2 can be applied.

In the above embodiment 1, the variations 1 to 5 of the embodiment 1, the above embodiment 2 and the variations 1 to 3 of the embodiment 2 according to the present invention, the forceps 2, 2A of the treatment devices 1, 1A may be applied to forceps 50 in the construction suitable for a surgery under endoscope as shown in FIG. 24, which will be described later.

The construction of the so constructed forceps 50 will be described. As shown in FIG. 24, the forceps 50 comprises a narrow and lengthy insertion sheath portion 51, an operation portion 52 connected to the base end of this insertion sheath portion 51 and a treatment portion 53 provided at the tip end of the insertion sheath portion 51.

The operation portion 52 has a fixed handle 54 and a movable handle 56 mounted to this fixed handle 54 capable of rotational movement through a handle pivotally support shaft 55. At the upper end of the fixed handle 54, an operation portion body 57 is integrally formed. At this operation portion body 57, the insertion sheath portion 51 is mounted rotatably in the direction around axis.

The insertion sheath portion 51 has a lengthy outer tube 58. In this outer tube 58, an elongated rod-state driving shaft 59 is inserted capable of advance/retreat in the axial direction. The base end of this driving shaft 59 is connected to the upper end of the movable handle 56 capable of rotational movement.

Therefore, when the movable handle 56 is rotated around the handle pivotally support shaft 55, an operation force acts on the driving shaft 59 and this driving shaft 59 moves back and forth in the axial direction.

The treatment portion 53 has a pair of jaws 60, 61 capable of opening/closing. The tip end portion of the driving shaft 59 is connected to the jaws 60, 61 through a driving mechanism, not shown. By this construction, by opening/closing operation of the movable handle 56, the jaws 60, 61 are opened/closed through the driving shaft 59.

The jaws 60, 61 are constructed in any one of the constructions of the above embodiment 1, the variations 1 to 5 of the embodiment 1, the above embodiment 2 and the variations 1 to 3 of the embodiment 2.

For example, if it is constructed as in the embodiment 1, the first electrode portion 19 and the second electrode portion 20 are provided at the jaw 60 at positions opposite to the jaw 61 in the state electrically insulated by the insulating member 25, respectively. Also, at the jaw 61, the receiving member 28 is integrally provided at a position opposite to the jaw 60.

Moreover, in the insertion sheath portion 51, the lead wires 21, 22 electrically connected to the first electrode portion 19 and the second electrode portion 20, respectively, as with the embodiment 1, are provided. And a cord connection portion 62 is provided at the operation portion body 57. To an inner end of this cord connection portion 62, the base ends of the lead wires 21, 22 are connected. Moreover, to the outer end of the cord connection portion 62, one end of a connection cord 63 is connected. The other end of this connection cord 63 is electrically connected to the power supply device 3 as with the embodiment 1.

The above construction was described for the case applied to the embodiment 1, but if it is applied to one of the other constructions of the variations 1 to 5 of the embodiment 1, the above embodiment 2 and the variations 1 to 3 of the embodiment 2, the first to the third electrode portions and the lead wires are also constructed according to the case as mentioned above.

Action when the living tissue is treated using the above constructed forceps 50 will be described.

When the living tissue is to be treated using the forceps 50 in FIG. 24, the operator introduces the treatment portion 53 and the tip end of the insertion sheath portion 51 of the forceps 50 through a trocar or the like, not shown, punctured into a body wall.

And the operator opens the movable handle 56 and operates to open the jaws 60, 61 as shown by a virtual line in FIG. 24 so as to position the living tissue between these jaws 60, 61. In that state, next, the operator operates the movable handle 56 in the closing direction so as to grip the living tissue between the jaw 60 and the jaw 61.

After gripping the living tissue, the operator selectively operates to turn on the first operation pedal 6, the second operation pedal 6 of the foot switch 5 so as to perform coagulation, incision of the living tissue as with the embodiment 1.

In this example, when the above embodiment 1 is applied, the high-frequency current flows between the two first electrode portion 19, the second electrode portion 20 from the power supply device 3 through the connection cord 63, the cord connection portion 62 and the lead wires 21, 22 as in the embodiment 1. When the embodiment 2 is applied, the high-frequency current flows between the respective electrode portions similarly to the construction and action in the embodiment 2.

Embodiment 3

Figure 25:
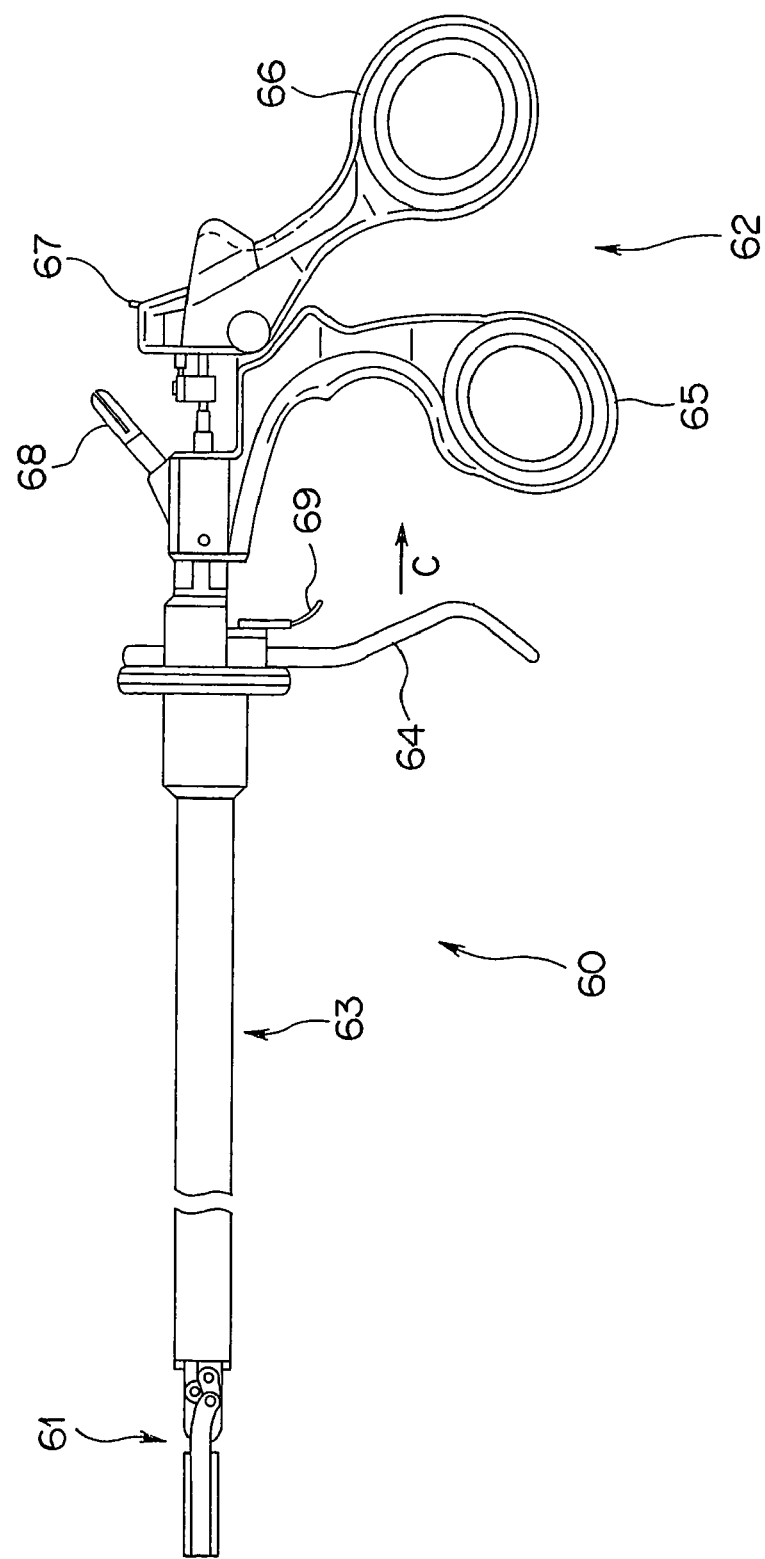
FIG. 25 is a side view showing the entire construction of the treatment device according to an embodiment 3 of the present invention.
Figure 26:
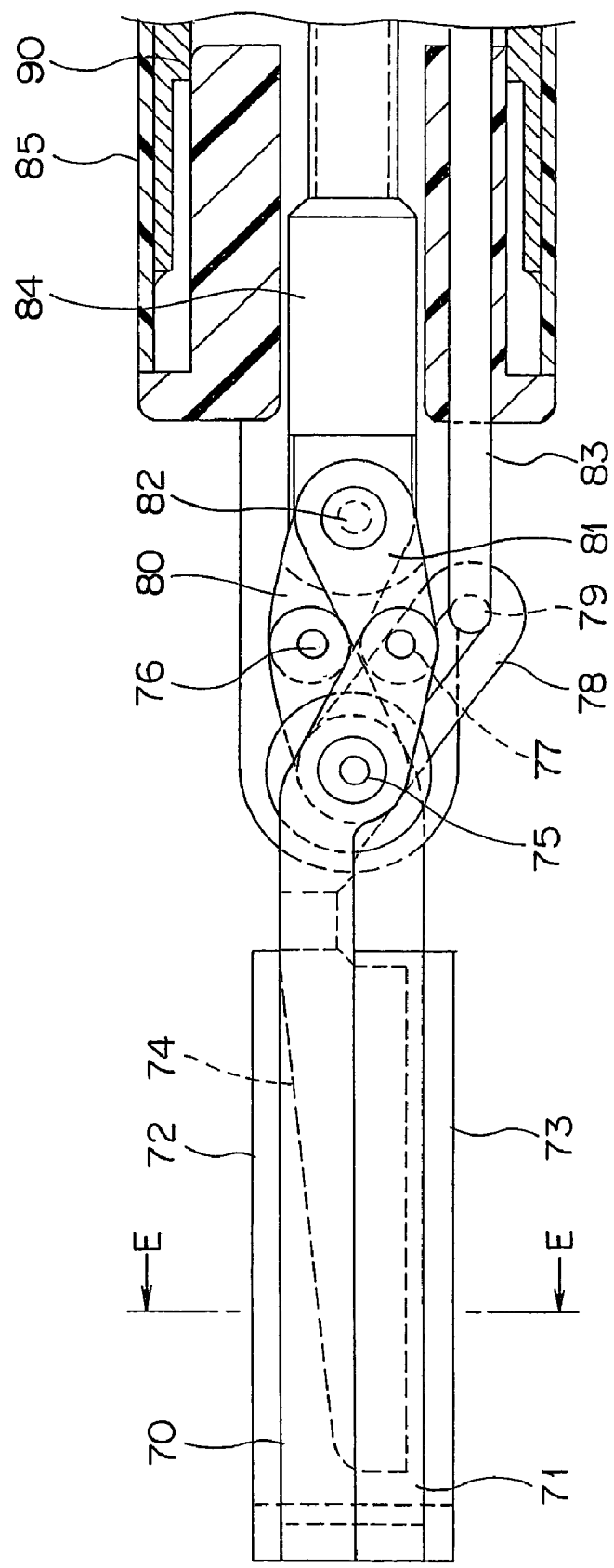
FIG. 26 is a configurational view of the treatment portion provided at the tip end side of an insertion portion of the treatment device.
Figure 27:
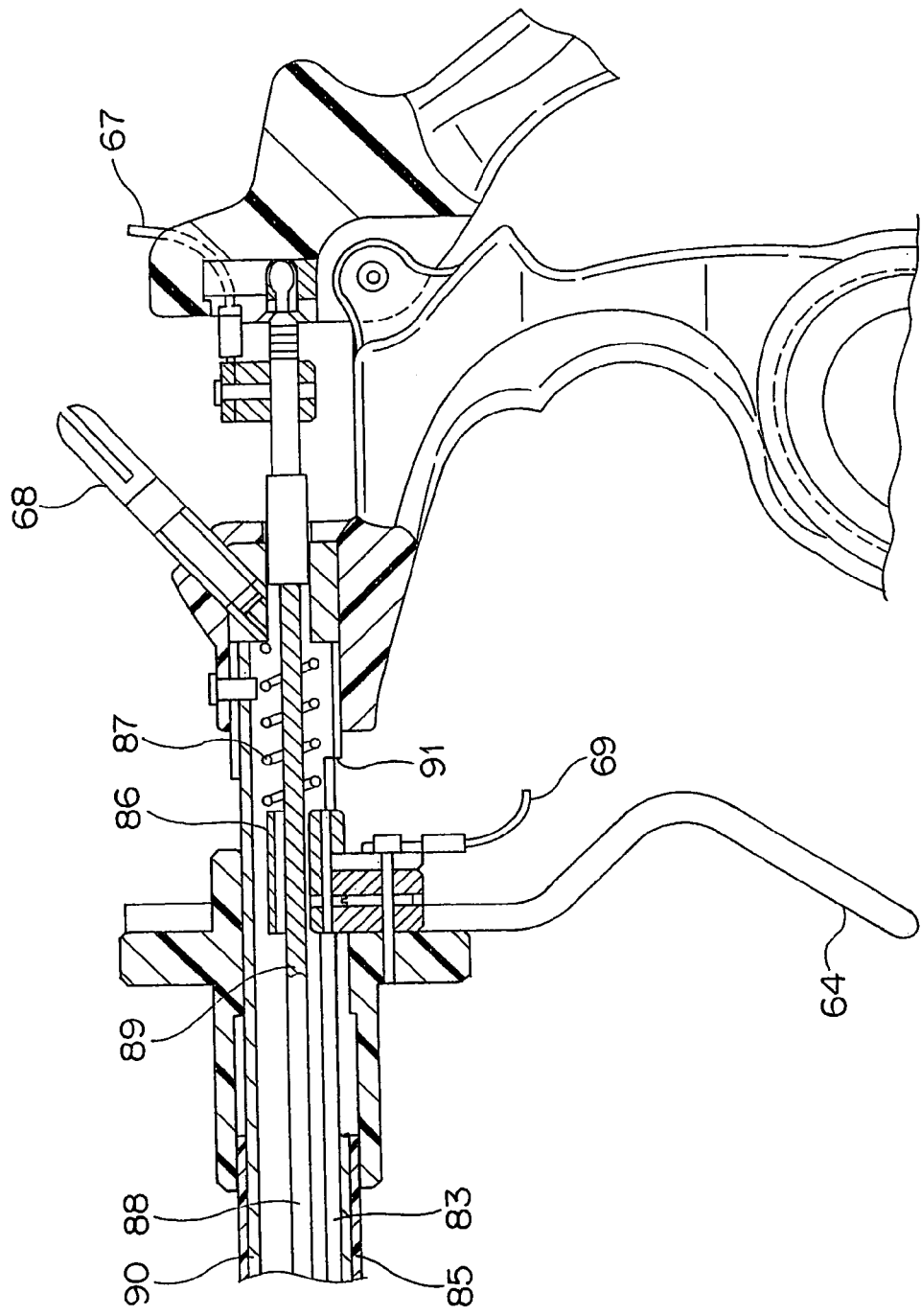
FIG. 27 is a configurational view of an operation portion showing a state before an operation lever of the operation portion is operated.
Figure 28:
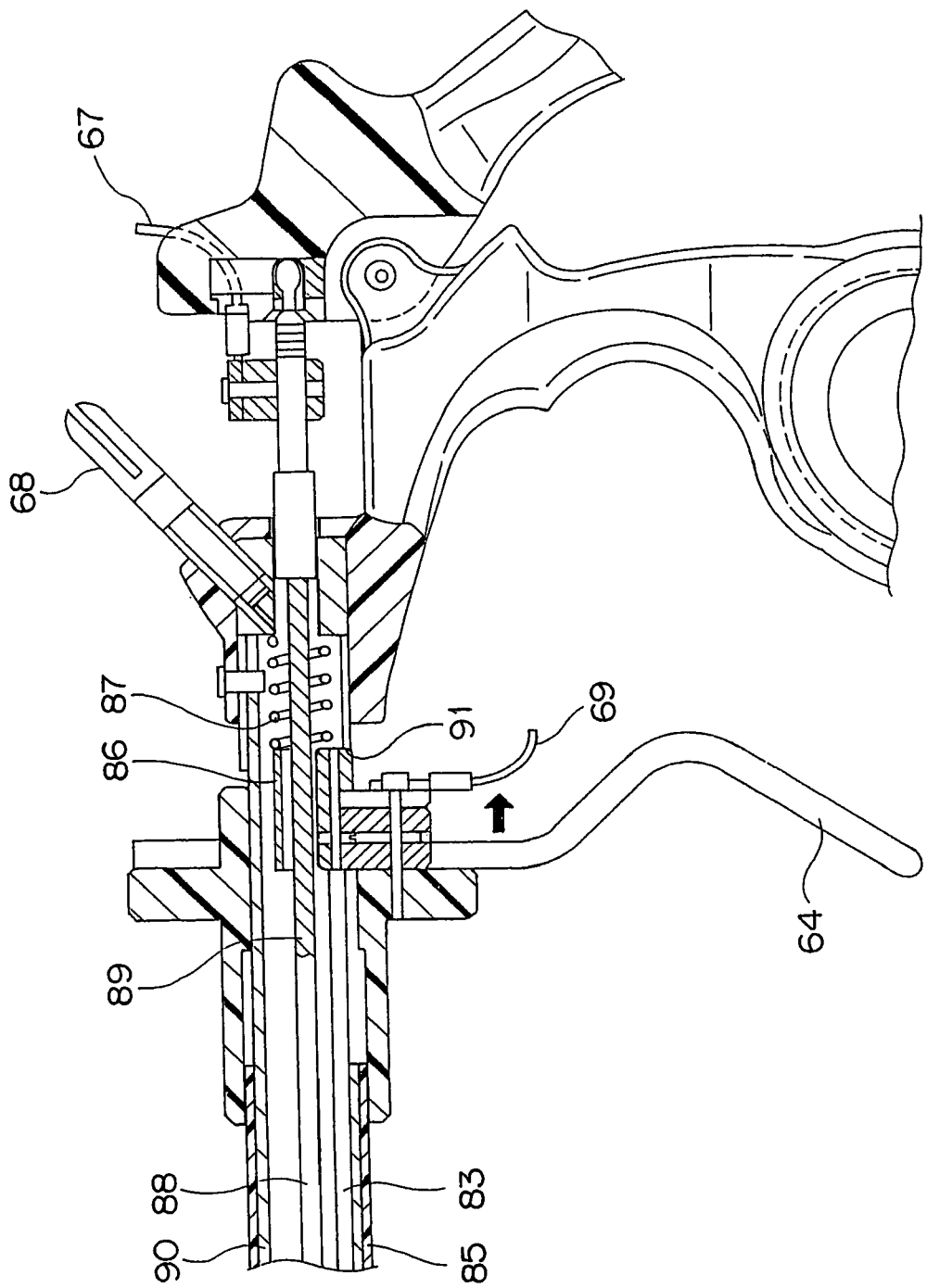
FIG. 28 is a configurational view of the operation portion showing a state where the operation lever is operated to the hand side from the state shown in FIG. 27.
Figure 29:
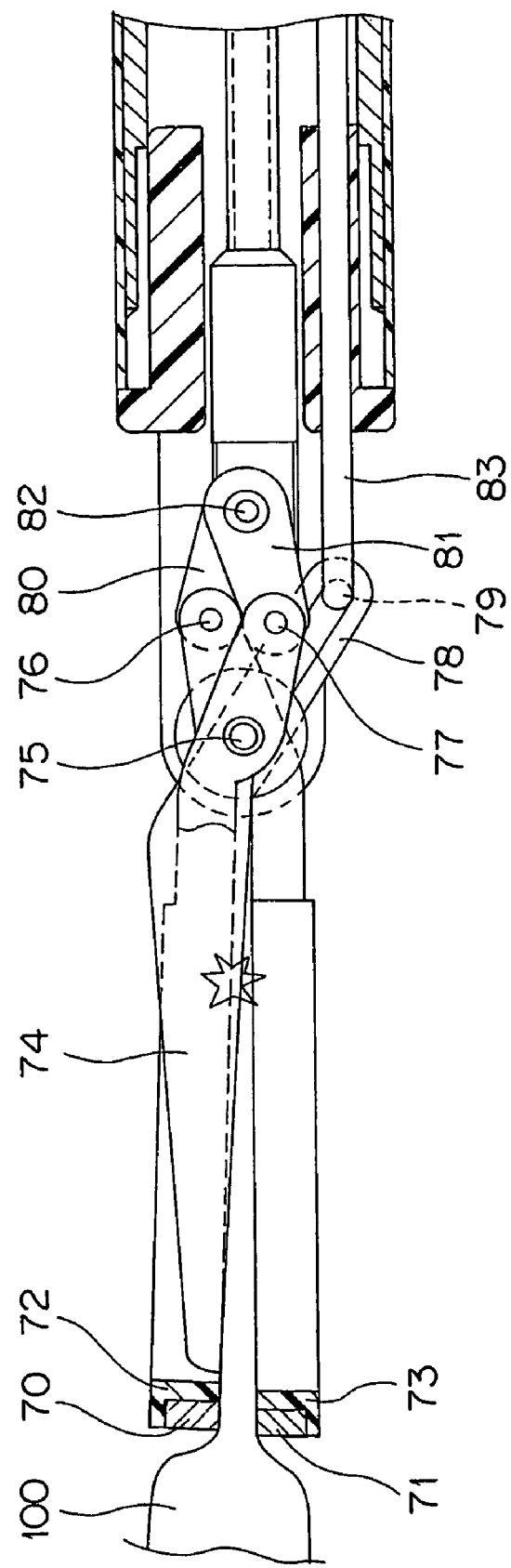
FIG. 29 is an explanatory view showing a state where the high-frequency current flows at the hand side of an electrode portion for incision to explain action of the electrode portion for incision by the treatment portion.
Figure 30:
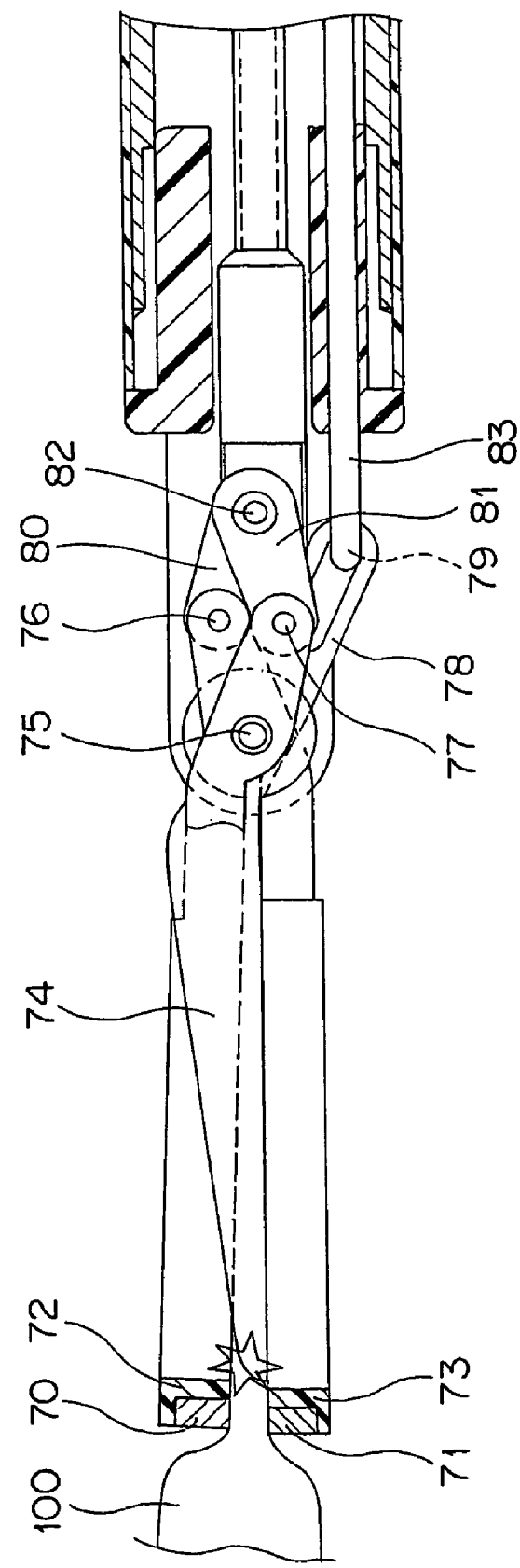
FIG. 30 is an explanatory view showing a state where the position where the high-frequency current flows is moved to the tip end side of the electrode portion for incision by an elastic force of an elastic member.
Figure 31:
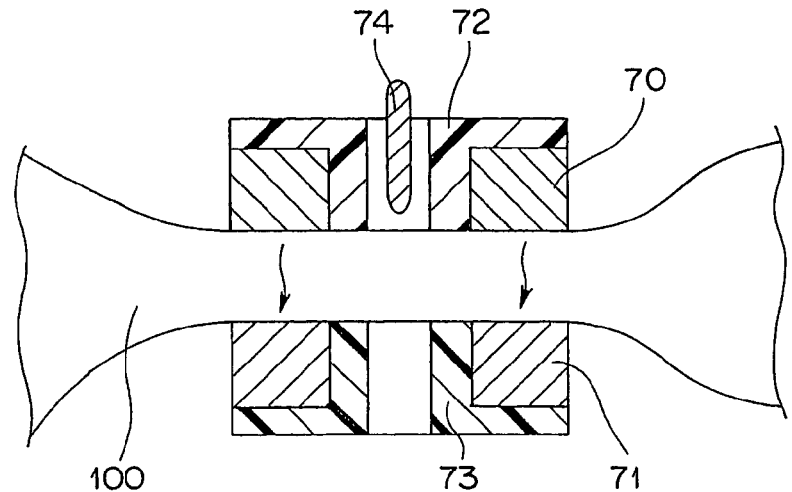
FIG. 31 is an explanatory view showing a state where the living tissue is coagulated to explain a treatment of the living tissue by the treatment device of the embodiment 3.
Figure 32:
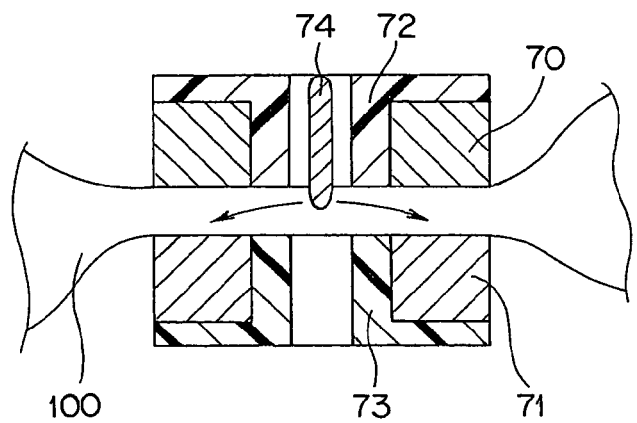
FIG. 32 is an explanatory view showing a state where the living tissue is incised by the electrode portion for incision.
Figure 33:
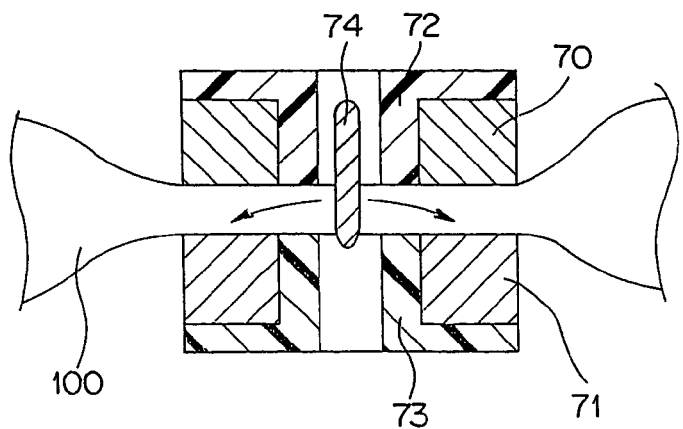
FIG. 33 is an explanatory view showing a state where the living tissue has been incised by the electrode portion for incision from the state shown in FIG. 32.

FIGS. 25 to 33 relate to an embodiment 3 of the present invention, in which FIG. 25 is a side view showing the entire construction of a treatment device according to the embodiment 3, FIG. 26 is a configurational view of a treatment portion provided at the tip end side of an insertion portion of the treatment device, FIGS. 27 and 28 are configurational views of an operation portion provided at the hand side of the treatment device, FIG. 27 shows a state before an operation lever of the operation portion is operated and FIG. 28 shows a state when the operation lever is operated to the hand side from the state shown in FIG. 27. Also, FIGS. 29 and 30 are explanatory views for explaining the action of an electrode portion for incision by the treatment portion, in which FIG. 29 shows a state where the high-frequency current flows at the hand side of the electrode portion for incision, and FIG. 30 shows a state where the position where the high-frequency current flows is moved to the tip end side of the electrode portion for incision by an elastic force of an elastic member, respectively. Moreover, FIGS. 31 to 33 show explanatory views for explaining a treatment of the living tissue by the treatment device of the embodiment 3, in which FIG. 31 shows a state where the living tissue is coagulated, FIG. 32 for a state where the living tissue is incised by the electrode portion for incision, and FIG. 33 for the state where the living tissue has been incised by the electrode portion for incision from the state in FIG. 32.

As shown in FIG. 25, a treatment device 60 of the embodiment 3 is constituted as a bipolar type coagulation incision tool and comprises a treatment portion 61 provided at the tip end portion for gripping the living tissue for coagulation and incision, an operation portion 62 to be held by an operator when using the treatment device 60, and an insertion portion 63 for connecting this operation portion 62 to the treatment portion 61 and guiding them into a body cavity.

At the operation portion 62, a movable handle 66 for opening/closing operation of a pair of coagulation gripping portions 70, 71 capable of opening/closing provided at the treatment portion 61, a holding handle 65 for holding the entire treatment device 60, and a lever 64 for operating an electrode portion 74 for incision, which will be described later, are provided. Moreover, at the operation portion 62, coagulation current conducting terminals 67, 68 for supplying a coagulating current to the coagulation gripping portions 70, 71 and an incision current conducting terminal 69 for supplying an incision current to en electrode portion 74 for incision are provided.

At the treatment portion 61, as shown in FIG. 26, the coagulation gripping portions 70, 71 and the incision electrode portion 74 are provided around a pin 75 capable of rotational movement. The pair of coagulation gripping portions 70, 71 are connected to a link member 80 and a link 81 at the hand side through pins 76 and 77 capable of rotational movement. The ling member 80 and the link member 81 are connected to a connecting member 84 provided at the distal end of a coagulation gripping portion driving member 88 (See FIG. 27) connected to the movable handle 66 through a pin 82 capable of rotational movement.

The lever 64 is connected to a slotted hole 78 provided at the hand side of the incision electrode portion 74 through an incision electrode driving shaft 83, an engagement portion 79. At the base end of the lever 64, as shown in FIG. 27, an abutting member 86 formed of an insulating material movable in the longitudinal axis direction is provided around the coagulation gripping portion driving shaft 88. This abutting member 86 is urged to the tip end side by an elastic member 87 in a coil spring state. The elastic member 87 is not limited to the coil spring state but it may be so constructed so as to urge the abutting member 86 to the tip end side.

Moreover, the incision current conducting terminal 69, the incision electrode driving shaft 83, the engagement portion 79 and the incision electrode portion 74 comprising the slotted hole 78 are electrically connected. The pin 75 and the pin 82 are formed of an insulating material such as alumina, zirconia or the like, for example. Though not shown, the coagulation gripping portions 70, 71 and the incision electrode portion 74 are electrically insulated by an insulating member so that they do not conduct electricity to each other in the vicinity of the pin 75 and the pin 82.

The insertion portion 63 has, as shown in FIG. 27, its surface covered by an insulating tube 85 and a metal pipe 90 inside it is electrically connected to the coagulation gripping portion 70 and the coagulation current conducting terminal 68. The coagulation gripping portion driving shaft 88 connected to the connecting member 84 is covered by an insulating cover 89 over the entire length and electrically connected to the coagulation current conducting terminal 67, the link member 80 and the coagulation gripping portion 71.

Next, action of the treatment device of the embodiment 3 will be described referring to FIGS. 27 to 33.

In the treatment device 60, the connection cord 4 from the power supply device 3 in the embodiment 1 is connected to the coagulation current conducting terminals 67, 68 and the incision current conducting terminal 69 in advance.

First, the operator inserts the insertion portion 63 of the treatment device 60 into a body cavity and moves the treatment portion 61 to the vicinity of a living tissue to be incised/treated. And when the operator opens the movable handle 66 in the opening direction, the coagulation gripping portion driving member 88 is moved in the distal direction and the link member 80 and the link member 81 are rotationally moved in the opening direction around the pin 82 provided at the connecting member 84. As a result, the coagulation gripping portion 70 and the coagulation gripping portion 71 are opened around the pin 75.

In this state, the operator arranges the living tissue between the coagulation gripping portion 70 and the coagulation gripping portion 71 and closes the movable handle 66 and holds tight. Then, the coagulation gripping portion driving member 88 is moved in the proximate direction and the link member 80 and the link member 81 are rotationally moved in the closing direction around the pin 82 provided at the connecting member 84. As a result, the coagulation gripping portion 70 and the coagulation gripping portion 71 are rotationally moved around the pin 75 and closed.

In this state, when the operator turns on the foot switch 5 (first operation pedal 6, or the second operation pedal 7), the high-frequency current with the coagulation waveform is supplied from the power supply device 3 to the coagulation current conducting terminal 68 through the connection cord 4 and the high-frequency current with the coagulation waveform is further conducted from this coagulation current conducting terminal 68 through the metal pipe 90, the coagulation gripping portion 70 to the living tissue.

At this time, as shown in FIG. 31, the high-frequency current with the coagulation waveform conducting from the coagulation gripping portion 70 to the living tissue 100 flows to the other coagulation gripping portion 71, and the living tissue 100 is coagulated by Joule heat when the current passes through the living tissue 100.

And the high-frequency current having flown to the coagulation gripping portion 71 reaches the link member 80, the coagulation gripping portion driving member 88, the coagulation current conducting terminal 67 and is recovered by the power supply device 3. After the living tissue 100 is sufficiently coagulated, when the foot switch 5 is operated to supply the high-frequency current with the incision waveform from the power supply device 3 to the incision current conducting terminal 69, the high-frequency current with the incision waveform flows to the living tissue 100 having been coagulated in advance through the incision electrode driving shaft 83, the engagement portion 79, the incision electrode portion 74.

At the same time, when the operator pulls the lever 64 to the hand side and holds it tight, since the incision electrode driving shaft 83 is moved to the hand side as shown in FIG. 29, an angle formed by the slotted hole 78 with respect to the longitudinal axis direction becomes smaller and the incision electrode portion 74 is closed.

And when the operator holds tight the lever 64 till the abutting member 86 abuts an abutting portion 91 and keeps this state as shown in FIGS. 27 and 28, a spark position by the incision waveform is moved from the hand side (See FIG. 29) to the tip end side (See FIG. 30) by a given elastic force urged by the elastic member 87. In this state, as shown in FIGS. 31 to 33, the incision electrode portion 74 gradually cuts into the living tissue 100. As a result, the living tissue 100 is incised with sufficient coagulation as shown in FIG. 33.

The high-frequency current with the incision waveform reaches from the living tissue 100 to the coagulation gripping portion 71, the link member 80, the coagulation gripping portion driving member 88, the coagulation current conducting terminal 67 and is finally recovered by the power supply device 3. Also, since the insulating members 72, 73 are provided at the coagulation gripping portions 70, 71, the high-frequency current with the incision waveform supplied from the incision electrode portion 74 does not directly flow to the coagulation gripping portions 70, 71 but is surely supplied to the living tissue 100.

Therefore, according to the embodiment 3, since the incision operation can be performed automatically by keeping a certain force by the elastic member 87, a constant incision operation can be performed easily all the time irrespective of the experience of the operator. Thus, time is not required for coagulation, incision operation of the living tissue and manipulability can be improved.

Figure 34:
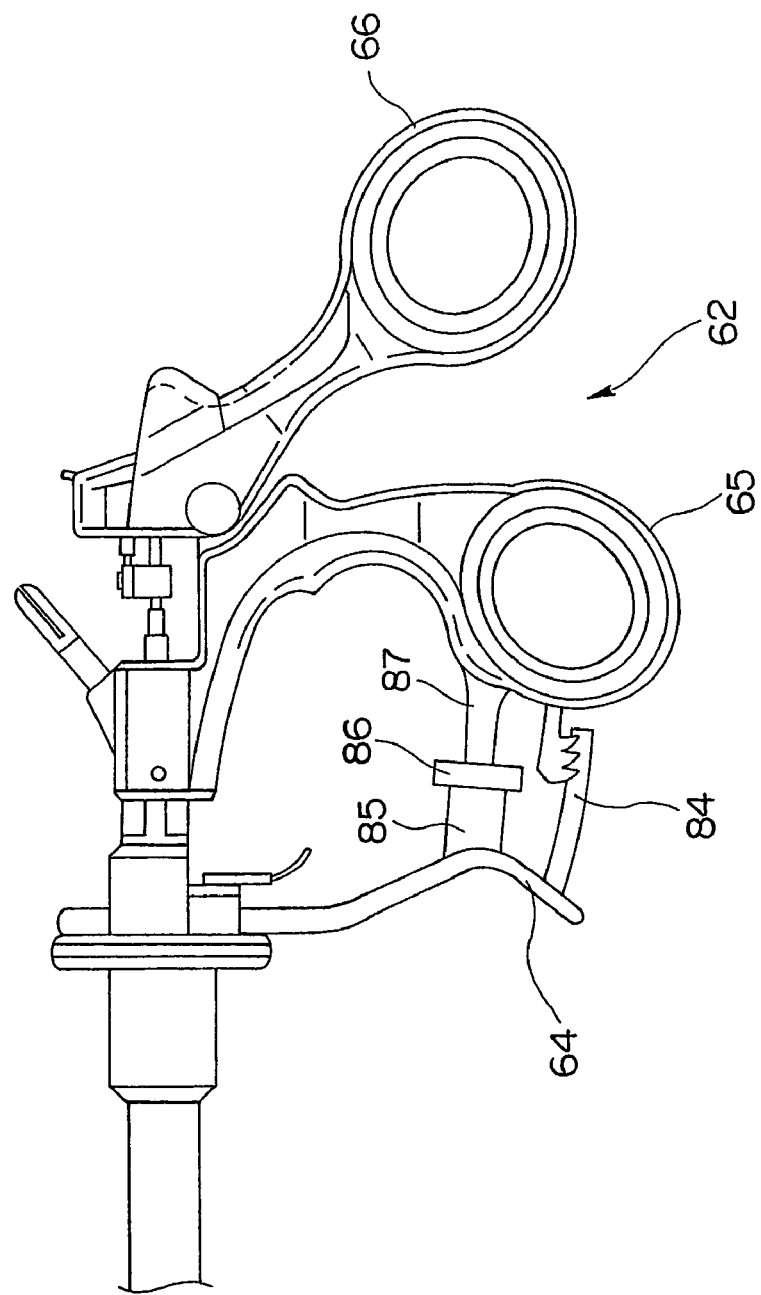
FIG. 34 is a side view showing a specific construction of the treatment device according to a variation of the embodiment 3.

The treatment device 60 according to the embodiment 3 may be constituted as a variation shown in FIG. 34. FIG. 34 is a side view showing a specific construction of a treatment device according to a variation of the embodiment 3.

That is, the treatment device 60 of the embodiment 3 comprises, as shown in the variation of FIG. 34, a latchet 84 is provided to be engaged with the holding handle 65 when holding tight the lever 64 of the operation portion 62 instead of the abutting portion 86 and the elastic member 87, and the abutting member 86 to abut against a projection portion 87 provided at the holding handle 65 is fixed to the lever 64 by an adhesive or the like at the elastic member 85 formed of rubber or the like so that a reaction force acts from the holding handle 65.

By this construction, since the incision electrode portion 74 can be held in the urged state with a certain force by holding tight the lever 64, the living tissue 100 can be incised even after releasing hold of the lever 64.

Embodiment 4

Figure 35:
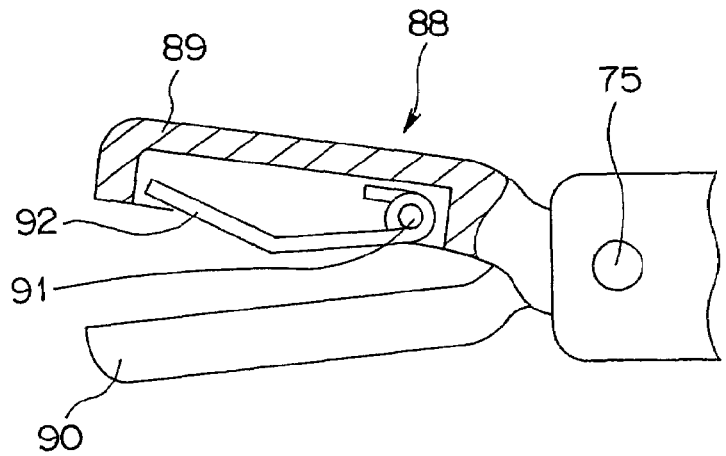
FIG. 35 is a sectional view showing a construction of a treatment portion of a treatment device according to an embodiment 4 of the present invention.
Figure 36:
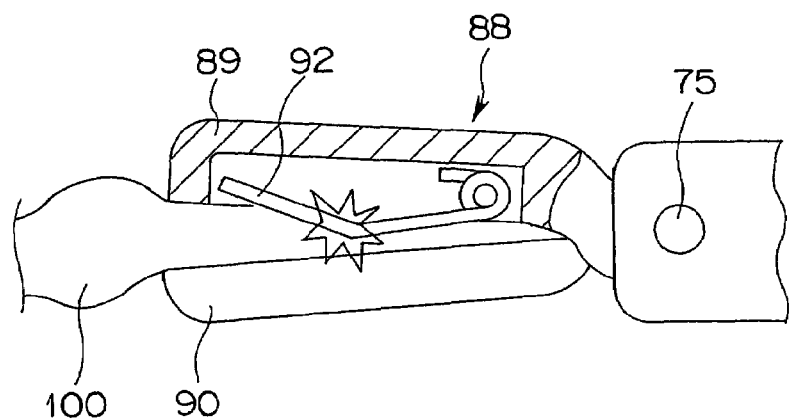
FIG. 36 is an explanatory view showing a state where the high-frequency current flows at the center part of the electrode portion for incision to explain a treatment of the living tissue by the treatment portion.
Figure 37:
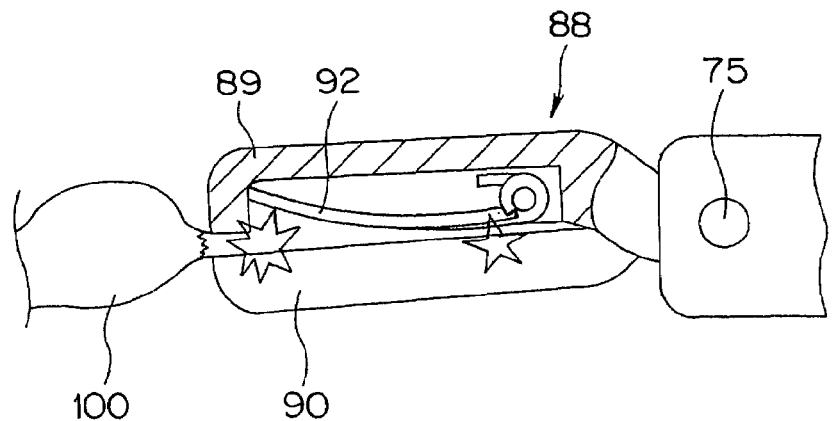
FIG. 37 is an explanatory view showing a state where the position where the high-frequency current flows is moved to the tip end side and the hand side of the electrode portion for incision by the elastic force.

FIGS. 35 to 37 relate to an embodiment 4 of the present invention, in which FIG. 35 is a sectional view showing a construction of a treatment portion of a treatment device according to the embodiment 4, FIGS. 36, 37 are explanatory views for explaining a treatment of a living tissue by the treatment portion, FIG. 36 shows a state where the high-frequency current flows at the center part of an incision electrode portion, and FIG. 37 shows a state where a position where the high-frequency current flows is moved to the tip end side and the hand side of the incision electrode portion by an elastic force, respectively.

As shown in FIG. 35, a treatment device 88 of the embodiment 4 is constructed as a bipolar type coagulation incision tool and is improved to a construction particularly with the purpose of incision with regard to the treatment portion 61 of the treatment device 60 of the embodiment 1. The hand-side operation portion and the opening/closing mechanism are basically the same as those of the embodiment 1 and the explanation will be omitted.

The treatment device 88 has a pair of gripping portions 89, 90 mounted at the treatment portion at the tip end of an insertion portion, capable of rotational movement with the pin 75 as the fulcrum, and an incision bar 92 is mounted capable of rotational movement at the gripping portion 89 with a pin 91 as the fulcrum in the state urged in a direction separated from the gripping portion 89.

This incision bar 92 is an elastic member and is formed with the middle part in the longitudinal direction bent at a dull angle so that its angle is directed to the gripping portion 90.

In this treatment device 88, the operator operates the movable handle of the operation portion, not shown, and holds the living tissue 100 between the pair of gripping portions 89, 90. At this time, in the state where a given gripping force is applied to the living tissue 100 by the gripping portions 89, 90, when the high-frequency current with the incision waveform is supplied to the gripping portion 89, since the gripping portion 89 and the incision bar 92 are electrically connected to each other, the high-frequency current with the incision waveform flows from the incision bar 92 through the living tissue 100 to the gripping portion 90.

Then, when the high-frequency current with the incision waveform is flows to the living tissue 100, Joule heat is locally generated and incision action is generated. At this time, the position of a spark generated at a bent portion close to the middle of the gripping portion 90 spreads to the front and rear by an elastic deformation action of the incision bar 92 with progress of the incision as shown in FIGS. 36 and 37. Then, the incision can be finally completed over the entire length of the gripped living tissue 100 (See FIG. 37).

In the embodiment 4, the gripping portion 90 may be constructed similarly to the coagulation gripping portion 71 having the insulating member 73 described in FIGS. 31 to 33 in the above embodiment 3.

Therefore, according to the embodiment 4, the living tissue can be incised by holding the living tissue 100 with the gripping portion 90 and supplying the high-frequency current with the incision waveform. The other effects are the same as those of the embodiment 3.

Figure 38:
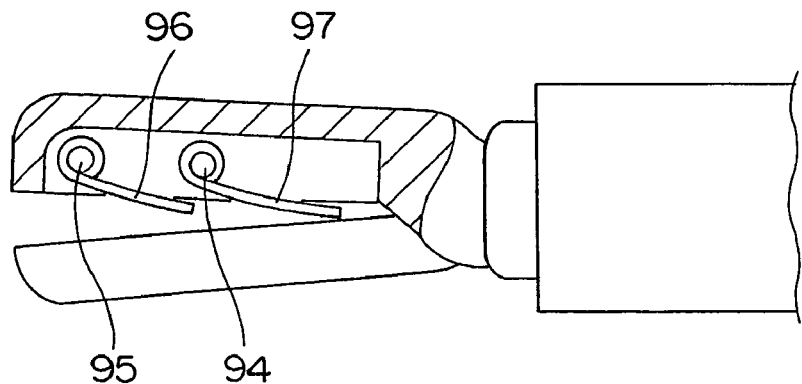
FIG. 38 is a sectional view showing a specific construction of a treatment device according to a variation of the embodiment 4.

The treatment device 88 of the embodiment 4 may be constructed as in a variation shown in FIG. 38. FIG. 38 is a sectional view showing a specific construction of the treatment device according to the variation of the embodiment 4.

That is, in the treatment device 88 of the embodiment 4, as in a variation shown in FIG. 38, an incision bar 96 and an incision bar 97 are provided capable of rotational movement with pins 94, 95 as fulcrums, respectively. By this construction, since the incision bars 96, 97 are short, incision can be performed in response to various shapes, thickness of the living tissue 100.

Embodiment 5

Figure 39:
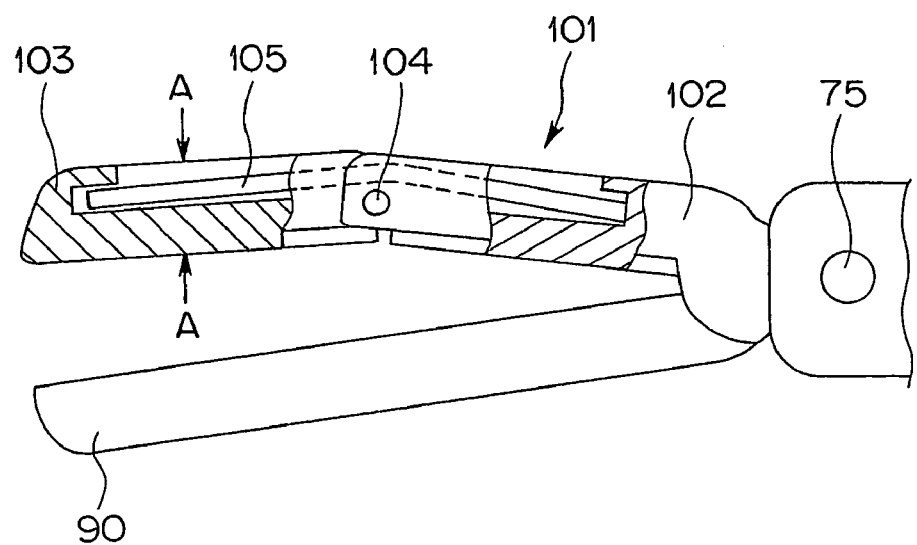
FIG. 39 is a sectional view showing a construction of a treatment portion of a treatment device according to an embodiment 5 of the present invention.
Figure 40:
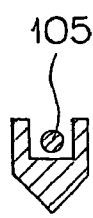
FIG. 40 is a sectional view taken on A-A line in FIG. 39.
Figure 41:
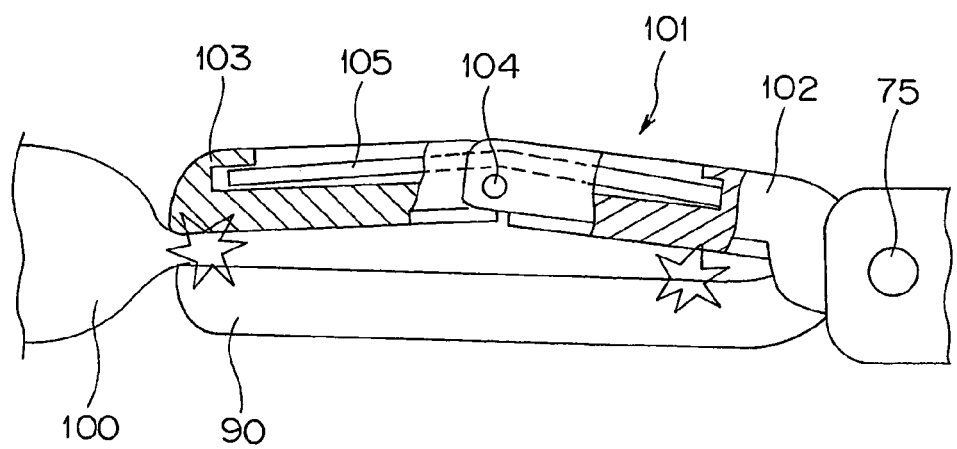
FIG. 41 is an explanatory view showing a state where the high-frequency current flows at the tip end side and the hand side of the treatment portion to explain a treatment of the living tissue by the treatment portion.
Figure 42:
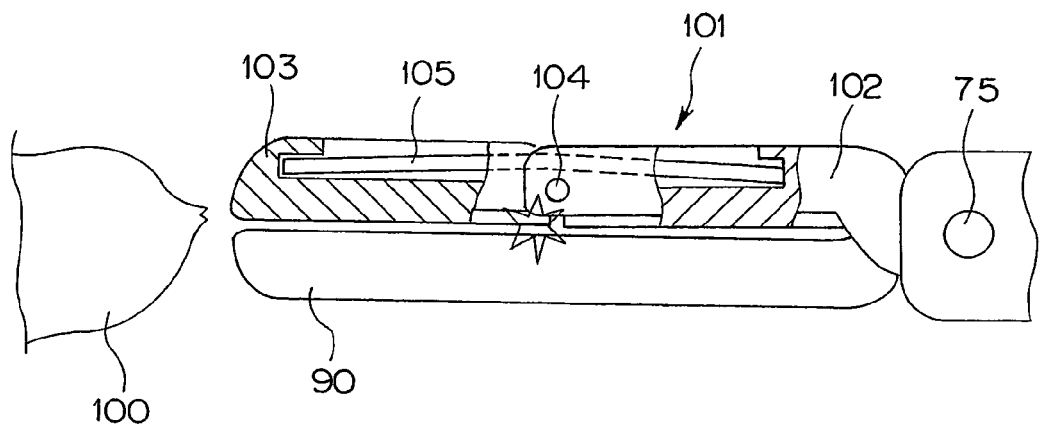
FIG. 42 is an explanatory view showing a state where the position where the high-frequency current flows is moved to the center part of the treatment portion by elastic force of a linear elastic body.

FIGS. 39 to 42 relate to an embodiment 5 of the present invention, in which FIG. 39 is a sectional view showing a construction of a treatment portion of a treatment device according to the embodiment 5, FIG. 40 is a sectional view taken on line A-A in FIG. 39, and FIGS. 41 and 42 are explanatory views for explaining a treatment of a living tissue, in which FIG. 41 shows a state where the high-frequency current flows to the tip end side and the hand side of the treatment portion, and FIG. 42 shows a state where a position where the high-frequency current flows is moved to the center part of the treatment portion by an elastic force of a linear elastic body.

As shown in FIG. 39, a treatment device 101 of the embodiment 5 is constructed as a bipolar type coagulation incision tool substantially similar to the treatment device 88 of the embodiment 4, and only differences will be explained.

The treatment device 101 has a hand-side gripping portion 102 and a tip-end side gripping portion 103 mounted at the upper gripping portion capable of rotational movement with a pin 104 as the fulcrum. Also, a linear elastic body 105 is mounted at upper parts of the hand-side gripping portion 102 and the tip-end side gripping portion 103 in the bent state urged in a direction separated from the gripping portion 90 in the vicinity of the center.

The hand-side gripping portion 102 and the tip-end side gripping portion 103 are electrically connected, and their sectional shapes are, as shown in FIG. 40, formed in the somewhat sharp shape on the gripping surface side.

In this treatment device 101, the operator operates the movable handle on the operation portion, not shown, so as to hold the living tissue 100 between the hand-side gripping portion 102, the tip-end side gripping portion 103 and the gripping portion 90. At this time, when the high-frequency current with the incision waveform is supplied to the hand-side gripping portion 102 and the tip-end side gripping portion 103 in the state a given gripping force is applied to the living tissue 100, the high-frequency current with the incision waveform flows from the hand-side gripping portion 102 and the tip-end side gripping portion 103 through the living tissue 100 to the gripping portion 90.

Then, when the high-frequency current with the incision waveform flows to the living tissue 100, Joule heat is locally generated and the incision action is generated. At this time, the position of a spark generated from the hand side portion of the hand-side gripping portion 102 proximate to the gripping portion 90 and the tip end portion of the tip-end side gripping portion 103 proximate to the gripping portion 90 is moved to the vicinity of the center by the elastic deformation action of the linear elastic body 105 with progress of the incision. Then, the incision can be finally completed over the entire length of the gripped living tissue 100 (See FIG. 42).

In the embodiment 5, the gripping portion 90 may be constructed similarly to the coagulation gripping portion 71 having the insulating member 73 explained in FIGS. 31 to 33 in the above embodiment 3.

Therefore, according to the embodiment 5, by holding the living tissue 100 between the respective gripping portions of the hand-side gripping portion 102, the tip-end side gripping portion 103 and the gripping portion 90 and by supplying the high-frequency current with the incision waveform, the living tissue 100 can be easily incised. The other effects are the same as those of the embodiment 4.

Figure 43:
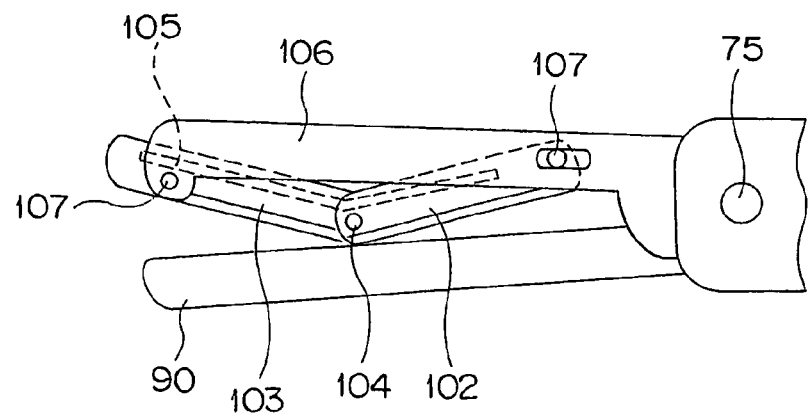
FIG. 43 is a sectional view showing a specific construction of a treatment device according to a variation of the embodiment 5.

The treatment device 101 of the embodiment 5 may be constructed as a variation shown in FIG. 43. FIG. 43 is a sectional view showing a construction of a treatment device according to the variation of the embodiment 5.

That is, in the treatment device 101 of the embodiment 5, the hand-side gripping portion 102 and the tip-end side gripping portion 103 are provided capable of rotational movement through a pin 104 and a pin 107 at the tip end and the base end of a support member 106 provided capable of rotational movement at the pin 75, and the center part is urged by the linear elastic body 105 so as to protrude to the gripping portion 90 side. According to this construction, since the respective gripping portions 102, 103 can be surely supported by the support member 106, the living tissue 100 can be firmly held for incision even if it is relatively stiff.

The present invention is not limited to the above-mentioned embodiments 1 to 5 and the variations of the respective embodiments but various variations are possible without departing from the gist of the invention.

In this invention, it is apparent that various modifications different in a wide range can be made on this basis of this invention without departing from the spirit and scope of the invention. This invention is not restricted by any specific embodiment except being limited by the appended claims.

What is claimed is:

1. A treatment device having a pair of first and second jaws capable of opening/closing with respect to each other at a tip end portion comprising:
    a relatively blunt tissue pressing portion provided on a surface portion of the first jaw opposite the second jaw and having a projection portion projecting toward the second jaw side;
    a receiving member provided on a surface portion of the second jaw opposite the first jaw at a position opposite the tissue pressing portion; and
    a plurality of electrode portions comprising a first electrode portion, a second electrode portion and a third electrode portion, the first and the third electrode portions being provided at the first jaw and the second electrode portion being provided at the second jaw, so that a high-frequency current flows through a living tissue compressed by the tissue pressing portion and the receiving member, wherein
    the first electrode portion is formed by the projection portion alone of the tissue pressing portion of the first jaw,
    the third electrode portion is formed so as to cover an insulating member electrically insulated by the projection portion and to be exposed on the surface of the second jaw side, and
    the second electrode portion is provided at the second jaw so as to hold the receiving member formed of the insulating member.

2. The treatment device according to claim 1, wherein
    the third electrode portion and the second electrode portion form a first current path so that a high-frequency current flows through a living tissue compressed by the tissue pressing portion and the receiving member; and
    the first electrode portion and the second electrode portion form a second current path so that the high-frequency current flows through the living tissue compressed by the tissue pressing portion and the receiving member.

3. The treatment device according to claim 2, further comprising switching means so that the high-frequency current flows through the first current path and the second current path at the same time or in a switching manner.

4. The treatment device according to claim 3, wherein the switching means is capable of selectively switching the supply of a high-frequency current with an incision waveform and a high-frequency current with a coagulation waveform.

* * * * *